US012752808B2

(12) United States Patent
Lim et al.

(10) Patent No.: US 12,752,808 B2
(45) Date of Patent: Oct. 6, 2026

(54) SYSTEM AND METHOD FOR ASSISTING DRIVER USING ELECTROENCEPHALOGRAM

(71) Applicant: HYUNDAI MOBIS CO., LTD., Seoul (KR)

(72) Inventors: Hyun Jun Lim, Seongnam-si (KR); Chang Won Lee, Seoul (KR); YuJin Jung, Seoul (KR); Jong Ho Hwang, Seoul (KR); June Seung Lee, Seoul (KR); Seong Ryul Park, Yongin-si (KR)

(73) Assignee: Hyundai Mobis Co., Ltd., Seoul (KR)

( * ) Notice: Subject to any disclaimer, the term of this patent is extended or adjusted under 35 U.S.C. 154(b) by 149 days.

(21) Appl. No.: 18/487,382

(22) Filed: Oct. 16, 2023

(65) Prior Publication Data

US 2024/0217533 A1 Jul. 4, 2024

(30) Foreign Application Priority Data

Jan. 4, 2023 (KR) ........................ 10-2023-0001311
Jul. 12, 2023 (KR) ........................ 10-2023-0090408

(51) Int. Cl.
*B60W 50/14* (2020.01)
*A61B 5/00* (2006.01)
(Continued)

(52) U.S. Cl.
CPC ............. *B60W 50/14* (2013.01); *A61B 5/165* (2013.01); *A61B 5/18* (2013.01); *A61B 5/374* (2021.01);
(Continued)

(58) Field of Classification Search
CPC ........ B60W 50/14; A61B 5/374; A61B 5/165; A61B 5/18; A61B 5/6815; A61B 5/7257; A61B 5/746
See application file for complete search history.

(56) References Cited

U.S. PATENT DOCUMENTS 5,813,993 A 9/1998 Kaplan et al.
2017/0303842 A1 10/2017 Yoshida et al.
(Continued)

FOREIGN PATENT DOCUMENTS

KR 10-2021-0103035 A 8/2021
KR 10-2022-0156699 A 11/2022

OTHER PUBLICATIONS

NIST Computer Security Resource Center via internet wayback machine "https://web.archive.org/web/20201128164520/https://csrc.nist.gov/glossary/term/application", "Application", 11/28/202, entire document.*

(Continued)

*Primary Examiner* — Hunter B Lonsberry
(74) *Attorney, Agent, or Firm* — NSIP Law

(57) ABSTRACT

A system for assisting a driver using an electroencephalogram includes an electroencephalogram measurer that measures an electroencephalogram signal of the driver, a mobile terminal that receives the measured electroencephalogram signal and outputs a careless state of the driver determined based on the received electroencephalogram signal via an app, and a controller that controls a vehicle based on the determined careless state of the driver and provides an alarm to the driver, and the mobile terminal includes a processor that analyzes a frequency component in the received electroencephalogram signal and quantifies the careless state of the driver using the analyzed frequency component. The driver assistance system analyzes the frequency component in the electroencephalogram signal of the driver measured
(Continued)

by the electroencephalogram measurer and quantifies the careless state of the driver using the analyzed frequency component.

14 Claims, 25 Drawing Sheets

(51) Int. Cl.
*A61B 5/16* (2006.01)
*A61B 5/18* (2006.01)
*A61B 5/374* (2021.01)

(52) U.S. Cl.
CPC .......... *A61B 5/6815* (2013.01); *A61B 5/7257* (2013.01); *A61B 5/746* (2013.01); *A61B 2503/22* (2013.01); *B60W 2050/146* (2013.01); *B60W 2540/221* (2020.02); *B60W 2540/30* (2013.01); *B60W 2555/20* (2020.02)

(56) References Cited

U.S. PATENT DOCUMENTS

| | | | | |
|---|---|---|---|---|
| 2019/0038166 | A1 | 2/2019 | Tavabi et al. | |
| 2021/0169417 | A1* | 6/2021 | Burton | A61B 5/4857 |
| 2022/0160309 | A1* | 5/2022 | Poltorak | A61B 5/7264 |
| 2024/0174216 | A1* | 5/2024 | Kaneko | G01C 21/3833 |
| 2024/0188868 | A1* | 6/2024 | Lee | A61B 5/389 |
| 2024/0400114 | A1* | 12/2024 | Viviano | A61B 5/163 |

OTHER PUBLICATIONS

Extended European Search Report issued on Apr. 26, 2024, in counterpart European Patent Application No. 23205393.4. (11pages in English).

Kwon, Ji-Won, et al. "Intraoperative real-time stress in degenerative lumbar spine surgery: Simultaneous analysis of electroencephalography signals and heart rate variability: A pilot study." The Spine Journal 20.8, Feb. 6, 2020. (pp. 1203-1210).

* cited by examiner (a) (b)

500

700

| ELECTROENCEPHALOGRAM (FREQUENCY CHARACTERISTICS) | FREQUENCY RANGE |
|---|---|
| THETA (Theta) | 4~8Hz |
| SMR (Sensorimotor) | 12~15Hz |
| MID-BETA(mBeta) | 15~20Hz |

SYSTEM AND METHOD FOR ASSISTING DRIVER USING ELECTROENCEPHALOGRAM

CROSS-REFERENCE TO RELATED APPLICATIONS

Pursuant to 35 U.S.C. § 119(a), this application claims the benefit of earlier filing dates and right of priority to Korean Application No. 10-2023-0001311, filed on Jan. 4, 2023 and Korean Application No. 10-2023-0090408, filed on Jul. 12, 2023, the contents of which are hereby incorporated by reference herein in their entirety.

BACKGROUND

Field

The present disclosure relates to a system and a method for assisting a driver using an electroencephalogram that grant objectivity to determination on driver's carelessness via an electroencephalogram signal of the driver and provide an alarm to the driver when a careless state of the driver is determined.

Discussion of the Related Art

In general, in modern society, the number of casualties resulted from various traffic accidents is increasing along with an explosive increase in vehicles caused by an increase in income and a pursuit of convenience of consumers. To minimize such casualties in the traffic accidents, many countries around the world are making great efforts to develop safety vehicles.

Such a safety vehicle refers to a vehicle that reduces fatalities in the event of the traffic accident, reduces fatigue of a driver, and is convenient to drive. A basic concept thereof is to prevent the accidents in advance to improve safety of the vehicle and protect a pedestrian.

Recently, to provide a more convenient interface to a user, a development of a human-friendly interface using a voice, a facial expression, a gesture, and a bio-signal such as an electroencephalogram, an electrooculogram, and an electromyogram has been attempted.

The electroencephalogram, the representative bio-signal, refers to a bio-signal that directly or indirectly reflects a person's conscious or unconscious state, and refers to a wave that is measured in all areas of a human scalp and mainly has a frequency equal to or lower than 50 Hz with a potential difference of several tens of microvolts.

Such an electroencephalogram may be classified into a delta wave, a theta wave, an alpha wave, a beta wave, a gamma wave, and the like based on the frequency of the wave.

The delta wave is an electroencephalogram with a frequency equal to or lower than 4 Hz and typically appears in a normal sleep state. The theta wave is an electroencephalogram with a frequency in a range from about 4 to 8 Hz, appears mainly when mentally unstable or distracted, and occurs when in a drowsy state or falling asleep. The alpha wave is an electroencephalogram with a frequency in a range from about 8 to 12 Hz and mostly appears clearly when mentally stable and in a comfortable psychological state with eyes closed. The beta wave refers to an electroencephalogram with a frequency in a range from about 12 to 30 Hz, appears stronger when under stress, such as a little anxiety or tension, and mainly appears when paying more than a certain amount of attention. In addition, the gamma wave refers to an electroencephalogram with a frequency in a range from about 30 to 50 Hz and appears in states of extreme arousal and excitement.

As described above, the driver is required to have considerable concentration while driving the vehicle, and the accident resulting in damage to the vehicle and a human life occurs because of momentary carelessness of the driver during the driving. In addition, the carelessness of the driver causes a large-scale accident that not only damages himself, but also damages others.

In addition, because a frequency band, a spectral density, or the like of an electroencephalogram signal measured from the driver may be different for each driver, there is a limit in consistently determining a careless state of the driver via the electroencephalogram signal.

SUMMARY

This Summary is provided to introduce a selection of concepts in simplified form that are further described below in the Detailed Description. This Summary is not intended to identify key features or essential features of the claimed subject matter, nor is it intended to be used as an aid in determining the scope of the claimed subject matter.

The present disclosure provides a system and a method for assisting a driver using an electroencephalogram. More specifically, it is to provide a system and a method for assisting a driver that may grant objectivity to determination on carelessness of the driver by analyzing a frequency component in an electroencephalogram signal of the driver measured by an electroencephalogram measurer and quantifying a carelessness state of the driver using the analyzed frequency component.

In addition, it is to provide a system and a method for assisting a driver that may reduce carelessness of a driver by determining a careless state of the driver and outputting the same via an app on a mobile terminal, and controlling a vehicle to provide an alarm to the driver.

In addition, it is to provide a system and a method for assisting a driver that may grant accuracy to determination on carelessness of the driver by converting information that takes into account not only an electroencephalogram signal of the driver but also driving information of a mobility into big data.

In addition, it is to provide alarm information necessary for each situation by collecting/refining driving information acquired from a plurality of mobilities and an electroencephalogram signal for each driving information at a server end and providing a carelessness-related alarm.

In addition, it is to provide a wearable device whose performance is improved and whose weight is reduced by making up for shortcomings of the wearable device used for electroencephalogram measurement.

In addition, it is to provide a mobile terminal to which an app that considers electroencephalogram characteristics for each driver and processes an electroencephalogram signal based on an operation state is applied.

The problems to be solved by the present disclosure are not limited to the above, and other problems not mentioned will be clearly understood by those skilled in the art to which the present disclosure belongs from the description below.

A first aspect of the present disclosure provides a system for assisting a driver using an electroencephalogram including an electroencephalogram measurer that measures an electroencephalogram signal of the driver, a mobile terminal that receives the measured electroencephalogram signal and outputs a careless state of the driver determined based on the received electroencephalogram signal via an app, and a controller that controls a vehicle based on the determined careless state of the driver and provides an alarm to the driver, wherein the mobile terminal includes a processor that analyzes a frequency component in the received electroencephalogram signal and quantifies the careless state of the driver using the analyzed frequency component.

In one implementation of the first aspect, the processor may analyze the frequency component in the received electroencephalogram signal via a window size in a first time unit.

In one implementation of the first aspect, the processor may shift the window size into a second time unit on a time axis and analyze the frequency component based on the window size.

In one implementation of the first aspect, the analyzing of the frequency component by the processor may include classifying the frequency component by performing Fourier transform on the received electroencephalogram signal, and the classified frequency component may include at least one of theta, beta, or SMR frequencies.

In one implementation of the first aspect, the processor may use the classified frequency component to quantify the careless state of the driver into a numerical value.

In one implementation of the first aspect, the processor may determine the careless state of the driver by comparing the numerical value with a preset alertness value.

In one implementation of the first aspect, the mobile terminal may output at least one of an emoji, a text, a color, and the received electroencephalogram signal via the app.

In one implementation of the first aspect, the mobile terminal may output a navigation screen or the number of alarms provided to the driver via the app.

In one implementation of the first aspect, the controller may provide the alarm to the driver by controlling the vehicle, including at least one of a display, an interior light, an air conditioner, a seat, and a speaker of the vehicle.

A second aspect of the present disclosure provides a system for assisting a driver using an electroencephalogram including a wearable device that measures an electroencephalogram signal of the driver, a mobile terminal equipped with an app, wherein the app receives the electroencephalogram signal measured by the wearable device and a driving information signal acquired from a mobility, processes the received electroencephalogram signal and driving information signal and provides the processed electroencephalogram signal and driving information signal to a server, and receives carelessness alarm information converted into big data from the server, and a controller that controls the mobility based on the carelessness alarm information and provides a carelessness-related alarm to the driver.

In one implementation of the second aspect, the carelessness alarm information may include driving information acquired from a plurality of mobilities and information determined based on an electroencephalogram signal for each driving information.

In one implementation of the second aspect, the driving information signal may include at least one of a GPS signal, a moving path signal of the mobility, a time information signal, and a weather information signal.

In one implementation of the second aspect, the carelessness alarm information may include at least one of information on in which moving path or location carelessness occurs, information on in what time period the carelessness occurs, and information on under what weather the carelessness occurs.

In one implementation of the second aspect, the controller may provide the carelessness-related alarm to the driver based on at least one of a moving path, a time, and a weather corresponding to the carelessness alarm information.

In one implementation of the second aspect, the wearable device may include a measurer wearable on a left ear of the driver, and a functional member including a battery that supplies power to the measurer, and the functional member may be fixable to a body part other than the ear of the driver or a fixture.

In one implementation of the second aspect, the app may measure electroencephalogram characteristics of the driver using an electroencephalogram signal measured during a predetermined time period while the driver wears the wearable device and drives, and measure an electroencephalogram signal after the predetermined time period in consideration of the electroencephalogram characteristics of the driver.

A third aspect of the present disclosure provides a method for assisting a driver using an electroencephalogram including measuring, by an electroencephalogram measurer, an electroencephalogram signal of the driver, receiving, by a mobile terminal, the measured electroencephalogram signal and determining a careless state of the driver based on the received electroencephalogram signal, outputting, by an app installed on the mobile terminal, the determined careless state of the driver, and controlling, by a controller, a vehicle based on the determined careless state of the driver and providing an alarm to the driver, wherein the determining of the careless state of the driver includes analyzing a frequency component in the received electroencephalogram signal and quantifying the careless state of the driver using the analyzed frequency component.

In one implementation of the third aspect, the determining of the careless state of the driver may include analyzing the frequency component in the received electroencephalogram signal via a window size in a first time unit.

In one implementation of the third aspect, the window size may be shifted into a second time unit on a time axis and the frequency component may be analyzed based on the window size.

In one implementation of the third aspect, the analyzing of the frequency component may include classifying the frequency component by performing Fourier transform on the received electroencephalogram signal, and the classified frequency component may include at least one of theta, beta, and SMR frequencies.

The system and the method for assisting the driver using the electroencephalogram according to the present disclosure may grant the objectivity to the determination on the carelessness of the driver by analyzing the frequency component in the electroencephalogram signal of the driver measured by the electroencephalogram measurer and quantifying the carelessness state of the driver using the analyzed frequency component.

In addition, the carelessness of the driver may be reduced by determining the careless state of the driver and outputting the same via the app on the mobile terminal, and controlling the vehicle to provide the alarm to the driver.

In addition, the accuracy may be granted to the determination on the carelessness of the driver by converting the information that takes into account not only the electroencephalogram signal of the driver but also the driving information of the mobility into the big data.

In addition, the alarm information necessary for each situation may be provided by collecting/refining the driving information acquired from the plurality of mobilities and the electroencephalogram signal for each driving information at the server end and providing the carelessness-related alarm.

In addition, the wearable device whose performance is improved and whose weight is reduced by making up for the shortcomings of the wearable device used for the electroencephalogram measurement may be provided.

In addition, the mobile terminal to which the app that considers the electroencephalogram characteristics for each driver and processes the electroencephalogram signal based on the operation state is applied may be provided.

Additional scope of applicability of the present disclosure will become apparent from the detailed description below. However, because various changes and modifications within the spirit and scope of the present disclosure may be clearly understood by those skilled in the art, the detailed description and specific embodiments, such as preferred embodiments, of the present disclosure should be understood as being given only as examples.

Other features and aspects will be apparent from the following detailed description, the drawings, and the claims.

DETAILED DESCRIPTION

Description will now be given in detail according to exemplary embodiments disclosed herein, with reference to the accompanying drawings. The same or equivalent components may be provided with the same reference numbers, and description thereof will not be repeated. As used herein, the suffixes "module" and "part" are added or used interchangeably to facilitate preparation of this specification and are not intended to suggest distinct meanings or functions. In describing embodiments disclosed in this specification, relevant well-known technologies may not be described in detail in order not to obscure the subject matter of the embodiments disclosed in this specification. In addition, it should be noted that the accompanying drawings are only for easy understanding of the embodiments disclosed in the present specification, and should not be construed as limiting the technical spirit disclosed in the present specification. As such, the present disclosure should be construed to extend to any alterations, equivalents and substitutes in addition to those which are particularly set out in the accompanying drawings.

Although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, it will be understood that when an element is referred to as being "directly connected with" another element, there are no intervening elements present.

A singular representation may include a plural representation unless it represents a definitely different meaning from the context.

The terms such as "include" or "have" used herein are intended to indicate that features, numbers, steps, operations, elements, components, or combinations thereof used in the following description exist and it should be thus understood that the possibility of existence or addition of one or more different features, numbers, steps, operations, elements, components, or combinations thereof is not excluded.

Figure 1:
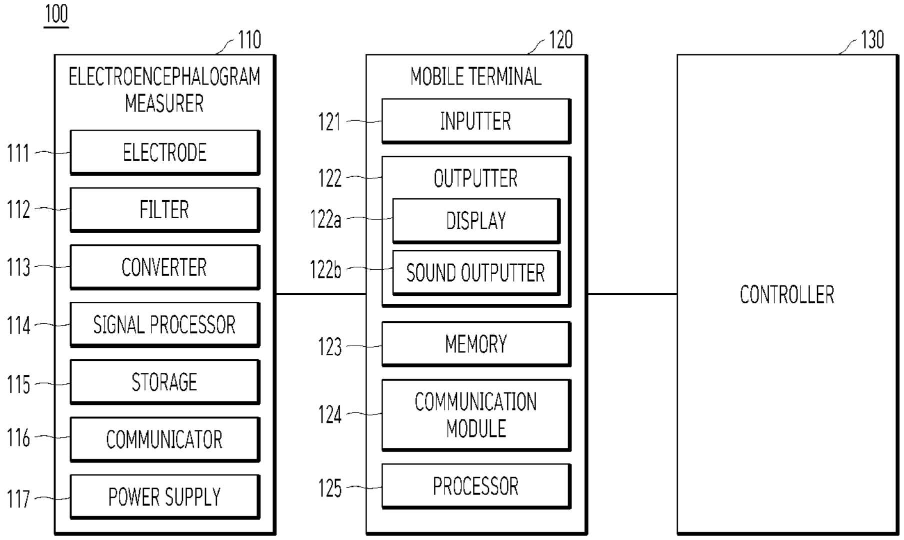
FIG. 1 is a block diagram of a driver assistance system according to an embodiment of the present disclosure.
Figure 2:
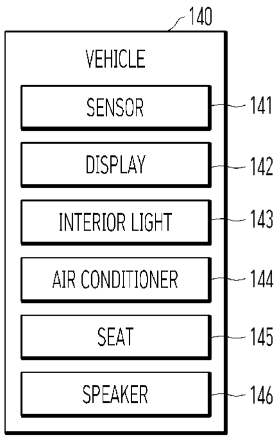
FIG. 2 is a diagram showing a configuration of a vehicle for providing an alarm to a driver from a driver assistance system according to an embodiment of the present disclosure.

FIG. 1 is a block diagram of a driver assistance system 100 according to an embodiment of the present disclosure. FIG. 2 is a diagram showing a configuration of a vehicle 140 for providing an alarm to a driver from the driver assistance system 100 according to an embodiment of the present disclosure.

The driver assistance system 100 according to one embodiment of the present disclosure may include an electroencephalogram measurer 110, a mobile terminal 120, and a controller 130 that controls the vehicle 140. In this regard, the electroencephalogram measurer 110 may include an electrode 111, a filter 112, a converter 113, a signal processor 114, storage 115, a communicator 116, and a power supply 117.

The driver assistance system 100 according to one embodiment of the present disclosure may measure an electroencephalogram signal of a driver via the electroencephalogram measurer 110. An electroencephalogram (EEG) is a phenomenon in which thoughts, emotions, and behaviors of an individual are generated by communication between nerve cells in a brain, and is a synchronized electrical wave generated when the nerve cells in the cerebral cortex transmit signals to each other. As described above, the electroencephalogram appears in various frequency bands, and is able to be specifically classified into a delta wave, a theta wave, an alpha wave, a beta wave, a gamma wave, and the like based on the frequency bands.

In this regard, the electroencephalogram measurer 110 may include an earset that is mounted around an ear of the driver and is able to measure an electroencephalogram signal around a left or right temporal lobe of the driver while driving. In another embodiment, the electroencephalogram measurer 110 may include a headset using a multi-channel electrode.

In addition, in the driver assistance system 100 according to one embodiment of the present disclosure, the electroencephalogram measurer 110 may include various sensors or equipment that may measure the electroencephalogram signal of the driver in real time, including the earset and headset described above.

The electrode 111 may measure the electroencephalogram signal of the driver during the driving and/or stopping of the driver in the vehicle 140 via an electrode. In this regard, the electrode 111 may include an EEG electrode, a REF electrode, and a GND electrode. The EEG electrode is a conductive electroencephalogram electrode, and is able to measure the electroencephalogram signal of the left or right temporal lobe by being in contact with an area near a left or right temporal lobe temple of the driver. The REF electrode is a reference electrode, and is able to provide a reference potential when the EEG electrode measures the electroencephalogram signal. The GND electrode is a ground electrode, is located on a back of an earflap, and is able to serve as a ground when the EEG electrode measures the electroencephalogram signal.

In one embodiment, the filter 112 may remove noise from the electroencephalogram signal of the driver measured by the electrode 111. The filter 112 may remove the noise from the electroencephalogram signal using a high pass filter, a low pass filter, or a band pass filter. As another embodiment, a filter such as a notch filter or an active filter may be used. In this regard, the noise may include noise generated by eye-blink of the driver, AC power noise, and a DC drift component as well as all elements that interfere with feature point extraction.

The converter 113 may convert the noise-removed electroencephalogram signal of the driver into a digital signal. The signal processor 114 may calculate one or more characteristics of the electroencephalogram from the electroencephalogram signal of the driver measured by the electroencephalogram measurer 110. The characteristics of the electroencephalogram calculated by the signal processor 114 may be, for example, at least one of a magnitude of the electroencephalogram signal in a time domain, a magnitude of the electroencephalogram signal in a frequency domain, and a magnitude of a signal-to-noise ratio (SNR) peak.

The storage 115 may store a reference electroencephalogram signal, that is, a preset alertness value, for determining a careless state of the driver based on the characteristics of the electroencephalogram. In this regard, the careless state of the driver may include a state in which the driver is not able to concentrate on the driving, including abnormal states such as drowsiness, reduced concentration, and surprise. In addition, the storage 115 may store the electroencephalogram signal of the driver measured via the electroencephalogram measurer 110 for a certain period of time. Such storage 115 may include an internal memory 123 and/or an external memory 123, and may include a volatile memory 123 such as a DRAM, a SRAM, or a SDRAM, a non-volatile memory 123 such as an one time programmable ROM (OTPROM), a PROM, an EPROM, an EEPROM, a mask ROM, a flash ROM, an NAND flash memory 123, or an NOR flash memory 123, and a storage device such as an SSD, a compact flash (CF) card, a SD card, a micro-SD card, a mini-SD card, an XD card, a flash drive such as a memory 123 stick, or an HDD.

The communicator 116 is a medium for transmitting and receiving information between the electroencephalogram measurer 110 and the mobile terminal 120 or the vehicle 140, and is able to transmit the electroencephalogram signal of the driver measured by the electroencephalogram measurer 110 to the mobile terminal 120 or the vehicle 140 via wireless communication. In the present embodiment, the communicator 116 may transmit and receive data with the mobile terminal 120 or the vehicle 140 via at least one communication among Bluetooth, radio frequency identification (RFID), infrared data association (IrDA), ultra-wideband (UWB), ZigBee, and wireless fidelity (Wi-Fi) technologies.

The power supply 117 may supply corresponding power throughout the electroencephalogram measurer 110. Specifically, the power supply 117 may include a converter that converts AC power to DC power and a DC/Dc converter that converts a level of the DC power. The power supply 117 may use a scheme of supplying the AC power via direct connection to an external power source, and may include a power supply 117 that includes a battery to be charged and used.

In the case of the former, a cable is connected to the power supply 117, so that it is difficult for the power supply 117 to move or a range of movement thereof is limited. In the case of the latter, the power supply 117 is free to move, but a weight and a volume thereof increase as much as those of the battery, and the power supply 117 must be directly connected to a power cable or coupled to a charging holder that supplies power for a certain period of time for charging. The charging holder may be connected to the electroencephalogram measurer 110 via a terminal thereof exposed to the outside, or the built-in battery may be charged when approaching the charging holder using a wireless scheme.

The mobile terminal 120 may include an inputter 121, an outputter 122, a memory 123, a communication module 124, and a processor 125. In this regard, the inputter 121 is for inputting video information (or signals), audio information (or signals), data, or information input by the user. When the information is input via the inputter 121, the processor 125 may control an operation of the mobile terminal 120 to correspond to the input information.

The outputter 122 is for generating an output related to a sense of sight, hearing, or touch, and is able to include a display **122*a* and a sound outputter 122*b*. In this regard, the display 122*a* may form a layer structure or may be integrally formed with a touch sensor. In addition, the sound outputter 122*b* may include a receiver, a speaker, a buzzer, and the like. In addition, information on the careless state of the driver, which will be described later, may be output via the outputter 122** and provided to the user.

The memory 123 may store data supporting various functions of the mobile terminal 120. The memory 123 may store a program for processing and controlling each signal within processor 125, and may store signal-processed video, sound, or data signals. For example, memory 123 may store an application program designed to perform various tasks that may be processed by the processor 125, and may selectively provide some of the stored application programs upon request from the processor 125.

The programs and the like stored in the memory 123 are not particularly limited as long as they may be executed by the memory 123. In addition, the memory 123 may perform a function for temporarily storing the video, audio, or data signals.

The memory 123 may include at least one of a volatile memory (e.g., a DRAM, a SRAM, a SDRAM, and the like) or a non-volatile memory (e.g., a flash memory, a hard disk drive (HDD), a solid-state drive (SSD), and the like).

The communication module 124 is a medium for transmitting and receiving information between the mobile terminal 120 and the electroencephalogram measurer 110 or the vehicle 140, and is able to receive the electroencephalogram signal of the driver measured by the electroencephalogram measurer 110 via the communication module 124 using wireless communication and is able to transmit the electroencephalogram signal to the vehicle 140.

The communicator 116 may transmit and receive wireless signals in a communication network based on wireless Internet technologies. In this regard, the wireless Internet technologies may include, for example, wireless LAN (WLAN), wireless-fidelity (Wi-Fi), wireless fidelity (Wi-Fi) direct, digital living network alliance (DLNA), wireless broadband (WiBro), world interoperability for microwave access (WiMAX), high speed downlink packet access (HSDPA), high speed uplink packet access (HSUPA), long term evolution (LTE), long term evolution-advanced (LTE-A), and the like.

In addition, the communicator 116 may support short-range communication using at least one of Bluetooth, radio frequency identification (RFID), infrared data association (IrDA), ultra wide band (UWB), ZigBee, near field communication (NFC), wireless-fidelity (Wi-Fi), Wi-Fi direct, and wireless universal serial bus (wireless USB) technologies.

Via a short-range wireless communication network, the wireless communication may be supported between the mobile terminal 120 and the communicator 116 of the electroencephalogram measurer 110, between the mobile terminal 120 and a wireless communication system, and between the mobile terminal 120 and a network where an external device is located. In addition, the above-mentioned short-range wireless communication network may be a short-range wireless personal area network.

The processor 125 may control all or some of the components included in the mobile terminal 120. Additionally, the processor 125 may control all or some of the components included in the mobile terminal 120 by running the application program stored in the memory 123.

In one embodiment, the processor 125 may determine whether the electroencephalogram measurer 110 is worn and, when the driver is not wearing the electroencephalogram measurer 110, generate a wearing recommendation signal to the driver to wear the electroencephalogram measurer 110. Such wearing recommendation signal maybe generated periodically until the driver wears the electroencephalogram measurer 110.

In addition, when the driver completes the driving, for example, when a transmission is placed in parking, the processor 125 may generate a removal recommendation signal to the driver to remove the electroencephalogram measurer 110 when the driver does not remove the electroencephalogram measurer 110. Such removal recommendation signal may be generated periodically until the driver removes the electroencephalogram measurer 110. In addition, the wearing recommendation signal and the removal recommendation signal generated by the processor 125 may be output via the outputter 122 of the mobile terminal 120 such that the driver may recognize the signals.

In particular, in the driver assistance system 100 according to one embodiment of the present disclosure, the processor 125 may analyze a frequency component of the electroencephalogram signal received via the communication module 124 and determine the careless state of the driver by quantifying the careless state of the driver using the analyzed frequency component. In addition, the controller 130 may control the vehicle 140 based on the determined careless state of the driver and provide an alarm to the driver.

FIG. 2 is a diagram showing a configuration of the vehicle 140 for providing the alarm to the driver, including a sensor 141, a display 142, an interior light 143, an air conditioner 144, a seat 145, and a speaker 146. In this regard, the sensor 141 located in the vehicle 140 may include all sensors located in the vehicle 140, including a brake sensor, a tilt sensor, a LiDAR sensor, a GPS sensor, and the like. Additionally, a behavior signal of the vehicle 140 may be input via the sensor 141, and driving of the components of the vehicle 140 may be sensed.

The driver assistance system 100 according to one embodiment of the present disclosure may control the vehicle 140 via the controller 130 and provide the alarm using stimulation to the driver in various ways. This may be provided via the display 142, the interior light 143, the air conditioner 144, the seat 145, and the speaker 146 located in the vehicle 140.

The controller 130 may provide the alarm to the driver via visual stimulation, including displaying a screen via the display 142 of the vehicle 140 or controlling the interior light 143 of the vehicle 140. In this regard, the display 142 may be a display device that includes all of a center information display (CID), a head up display (HUD), and the like.

The controller 130 may control an intensity of the interior light 143 or a wavelength of the interior light 143. The interior light 143 may be a mood light or an ambient light inside the vehicle 140. Additionally, the interior light 143 may include an LED installed above a cluster fascia of a driver's seat or installed on a side surface of the seat 145, and the controller 130 may control ON and OFF of LED power to provide the alarm to the driver via the visual stimulation.

The controller 130 may provide the alarm to the driver via olfactory stimulation, including controlling an indoor temperature via the air conditioner 144 of the vehicle 140 or introducing external air. For example, the controller 130 may control the indoor temperature by operating an air conditioner to lower the indoor temperature when concentration of the driver decreases. To lower a carbon dioxide concentration, the controller 130 may control external air to flow into the vehicle 140 in an external air circulation mode, and may control the air conditioner 144 to generate the olfactory stimulation to the driver using an air freshener and the like.

Additionally, the controller 130 may provide the alarm to the driver via tactile stimulation, including controlling at least one of a massage device, a ventilation device, or an adjustable device installed in the seat 145 of the vehicle 140.

Additionally, the controller 130 may provide the alarm to the driver via auditory stimulation, including outputting sound via the speaker 146 of the vehicle 140. In one embodiment, the speaker 146 may be located on a headrest of the seat 145 and provide the alarm to the driver via the auditory stimulation at a location close to both ears of the driver.

Figure 3:
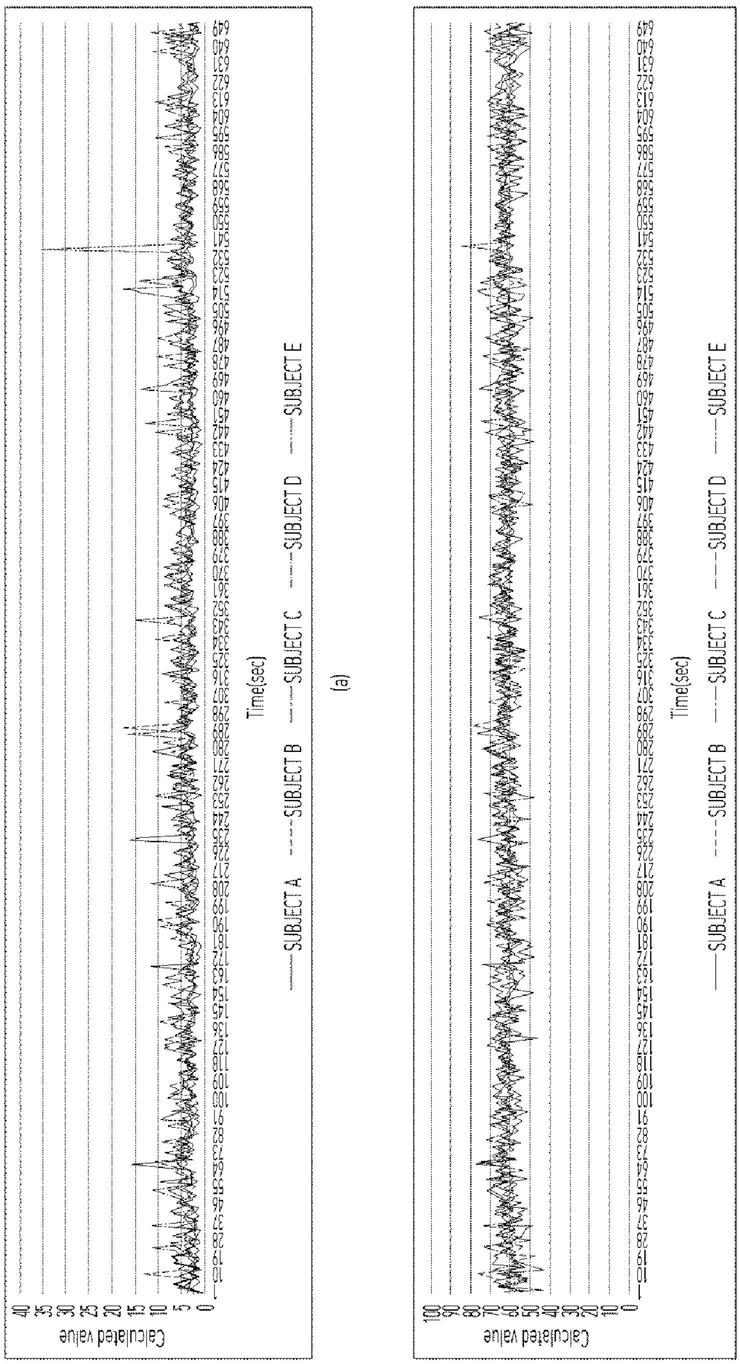
FIG. 3 is a diagram for illustrating granting objectivity in determining carelessness of a driver via a driver assistance system according to one embodiment of the present disclosure, compared to determining the carelessness of the driver via an electroencephalogram signal in prior art.

FIG. 3 is a diagram for illustrating granting objectivity in determining carelessness of a driver via the driver assistance system 100 according to one embodiment of the present disclosure, compared to determining the carelessness of the driver via an electroencephalogram signal in prior art.

As described above, because the frequency band, a spectral density, or the like of the electroencephalogram signal measured from the driver may be different for each driver, there is a limit in consistently determining the careless state of the driver via the electroencephalogram signal.

In relation, (a) in FIG. 3 shows an example of data for determining the carelessness of the driver via the electroencephalogram signal in prior art. Referring to (a) in FIG. 3, the carelessness of the driver was determined by performing four arithmetic operations on multiple types of measured electroencephalogram signals of the driver for respective frequencies. For example, the careless state of the driver was determined based on a value calculated by adding a voltage value of the beta wave and a voltage value of an SMR wave and dividing the obtained value by a voltage value of the theta wave.

However, as shown in (a) in FIG. 3, the frequency band, the spectral density, or the like of the measured electroencephalogram signal is different for each driver, so that the objectivity of the determination on the carelessness of the driver is not able to be guaranteed. In this case, reliability of the determination on the carelessness of the driver via the electroencephalogram signal is reduced and an unnecessary alarm is provided to the driver.

To solve the above-mentioned problem, the driver assistance system 100 according to one embodiment of the present disclosure is to ensure the objectivity of the determination on the carelessness of the driver regardless of the electroencephalogram signal that may be measured differently for each driver.

In other words, the frequency component of the electroencephalogram signal may be analyzed via the processor 125 described above with reference to FIG. 1 and the careless state of the driver may be quantified using the analyzed frequency component, thereby ensuring the objectivity of the determination on the carelessness of the driver.

In this regard, the processor 125 may classify the frequency component by performing Fourier transform on the received electroencephalogram signal. In this regard, The Fourier transform may be a concept that includes all of Fast Fourier Transform (FFT), Short Time Fourier Transform (STFT), and the like.

In one embodiment, the frequency component classified via the processor 125 in the driver assistance system 100 according to one embodiment of the present disclosure may include at least one of theta (θ) beta (β), or SMR frequencies. In addition, the careless state of the driver may be quantified via Mathematical Formula below using the classified frequency component.

(b) in FIG. 3 is data obtained by outputting in real time a value of the careless state of the driver quantified via Mathematical Formula below according to one embodiment of the present disclosure described above.

$$50.5 + 21.498 \times \ln\left(\frac{\beta + SMR}{\theta}\right) \quad \text{[Mathematical Formula]}$$

According to one embodiment of the present disclosure, the careless state of the driver may be quantified as a value from 0 to 100 via Mathematical Formula above. Therefore, compared to the data in prior art shown in (a) in FIG. 3, it may be seen that a deviation in the determination on the carelessness between the drivers is able to be reduced via the data for determining the carelessness of the driver according to one embodiment of the present disclosure shown in (b) in FIG. 3.

In addition, a time point at which the carelessness of the driver occurs may be objectively and accurately determined via the same, so that the reliability of the determination on the carelessness of the driver may be increased and the unnecessary alarm may be prevented, thereby efficiently providing the alarm to driver.

Figure 4:
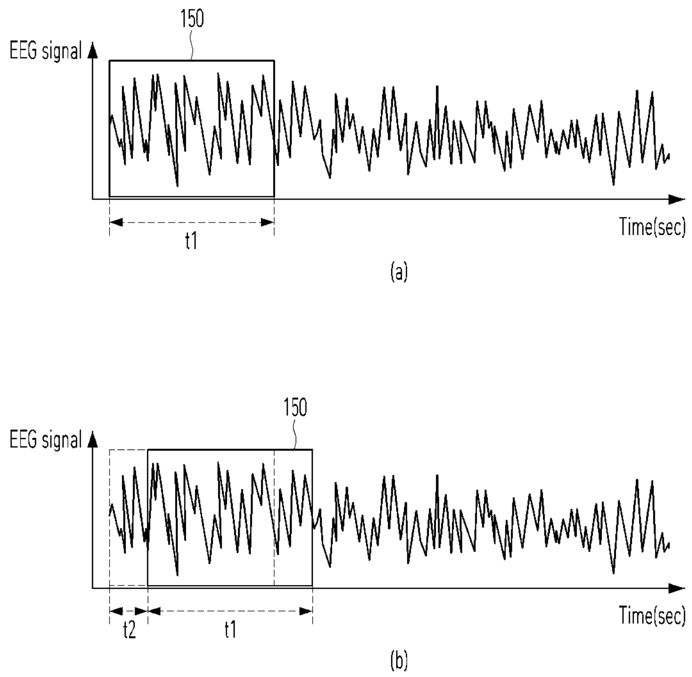
FIGS. 4 and 5 are diagrams for illustrating a scheme of analyzing a frequency component via a window size in a driver assistance system according to an embodiment of the present disclosure.
Figure 5:
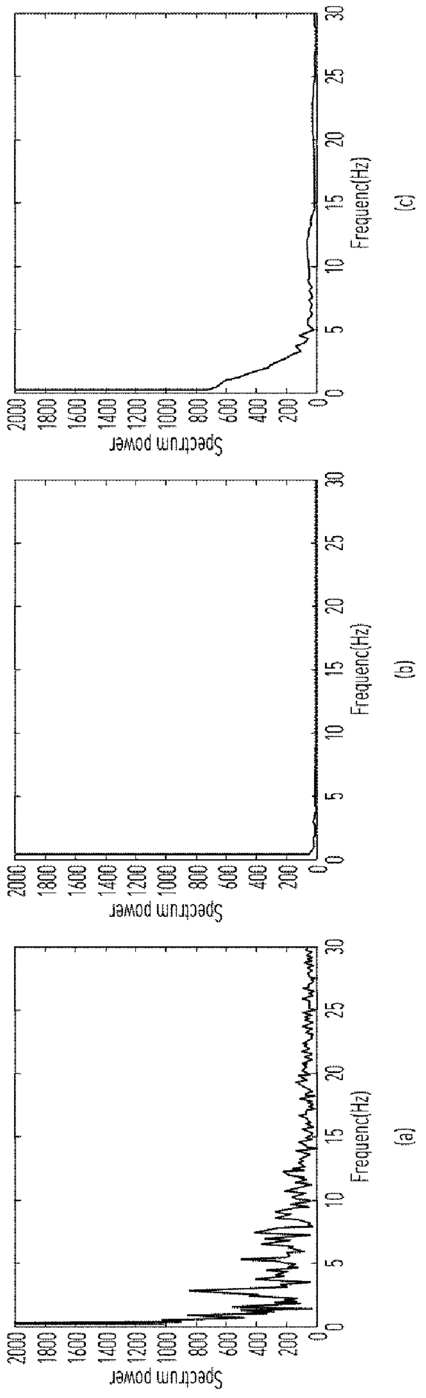

FIGS. 4 and 5 are diagrams for illustrating a scheme of analyzing a frequency component via a window size 150 in the driver assistance system 100 according to an embodiment of the present disclosure.

Referring to FIG. 1 together, the driver assistance system 100 according to one embodiment of the present disclosure may measure the electroencephalogram signal of the driver via the electroencephalogram measurer 110 and receive the electroencephalogram signal measured by the mobile terminal 120. In addition, the processor 125 may analyze the frequency component in the received electroencephalogram signal via the window size 150 in a first time unit. Additionally, the processor 125 may shift the window size 150 into a second time unit on a time axis and analyze the frequency component as much as the window size 150.

(a) in FIG. 4 is a diagram showing an example of analyzing the electroencephalogram signal via the window size 150 in the first time unit, and (b) in FIG. 4 is a diagram showing shifting the window size 150 into the second time unit on the time axis and analyzing the frequency component as much as the window size 150.

In this regard, according to one embodiment of the present disclosure, t1 may be 4 seconds and t2 may be 1 second. In other words, the frequency component may be analyzed in the electroencephalogram signal via the 4-second window size 150 and the 1-second shift.

In this regard, the analyzing of the frequency component by the processor 125 may include classifying the frequency component by performing the Fourier transform on the received electroencephalogram signal as described above, and the classified frequency component may include at least one of the theta, beta, or SMR frequencies.

Therefore, as shown in FIG. 4, the driver assistance system 100 according to one embodiment of the present disclosure may calculate an average value of theta, beta, and SMR frequency intensities for 4 seconds in the electroencephalogram signal via the 4-second window size 150 and the 1-second shift every second, and quantify the careless state of the driver via Mathematical Formula above.

In this regard, FIG. 5 is experimental data for determining a minimum unit of the window size 150, that is, a minimum first time unit, for extracting meaningful data of the electroencephalogram signal via the window size 150. (a) to (c) in FIG. 5 are drawings showing cases of extracting data from the electroencephalogram signal via a window size 150 in a 10-second unit, via a 2-second unit, and via a 4-second unit, respectively.

As shown in FIG. 5, it may be seen that the window size 150 in the 2-second unit is somewhat inappropriate for quantifying the careless state of the driver by analyzing the frequency component in the above-mentioned electroencephalogram signal.

Accordingly, the driver assistance system 100 according to one embodiment of the present disclosure may calculate the average value of the theta, beta, and SMR frequency intensities from the electroencephalogram signal every second via the window size 150 in the at least 4-second unit and quantify the careless state of the driver via Mathematical Formula above.

In addition, the processor 125 may determine the careless state of the driver by comparing the quantified value with the preset alertness value. As described above, according to one embodiment of the present disclosure, the careless state of the driver may be quantified as the value from 0 to 100 via Mathematical Formula above.

In this regard, the preset alertness value may be stored in the memory 123 as described above with reference to FIG. 1. In addition, the preset alertness value may be set, for example, by classifying a range equal to or lower than 55 into a range with poor alertness, a range from 56 to 80 into a range with good alertness, and a range from 81 to 100 into a range with the highest alertness.

Therefore, according to the above example, when the value quantified via Mathematical Formula above is 50, this corresponds to a section where the alertness is poor compared to the preset alertness value, which may be determined as the careless state of the driver. In addition, when the driver is determined to be in the careless state, the vehicle 140 may be controlled via the controller 130 to provide the alarm to the driver.

Additionally, as one embodiment of the present disclosure, continuous provision of the alarms to the driver may be restricted to prevent the unnecessary and excessive alarms from being provided to the driver. For example, after the alarm is provided to the driver, there may be a certain time interval until a next alarm is provided.

Additionally, as one embodiment of the present disclosure, the vehicle 140 may be controlled via the controller 130 such that more than the reference number of alarms are not provided within a reference time. In this case, when the reference time elapses, the reference number may also be initialized. That is, for example, when the reference time is 10 minutes and the reference number is 10 minutes, the alarm may not be provided more than 10 times in 10 minutes. In addition, the alarm may be provided by re-initializing the reference number every 10 minutes.

Figure 6:
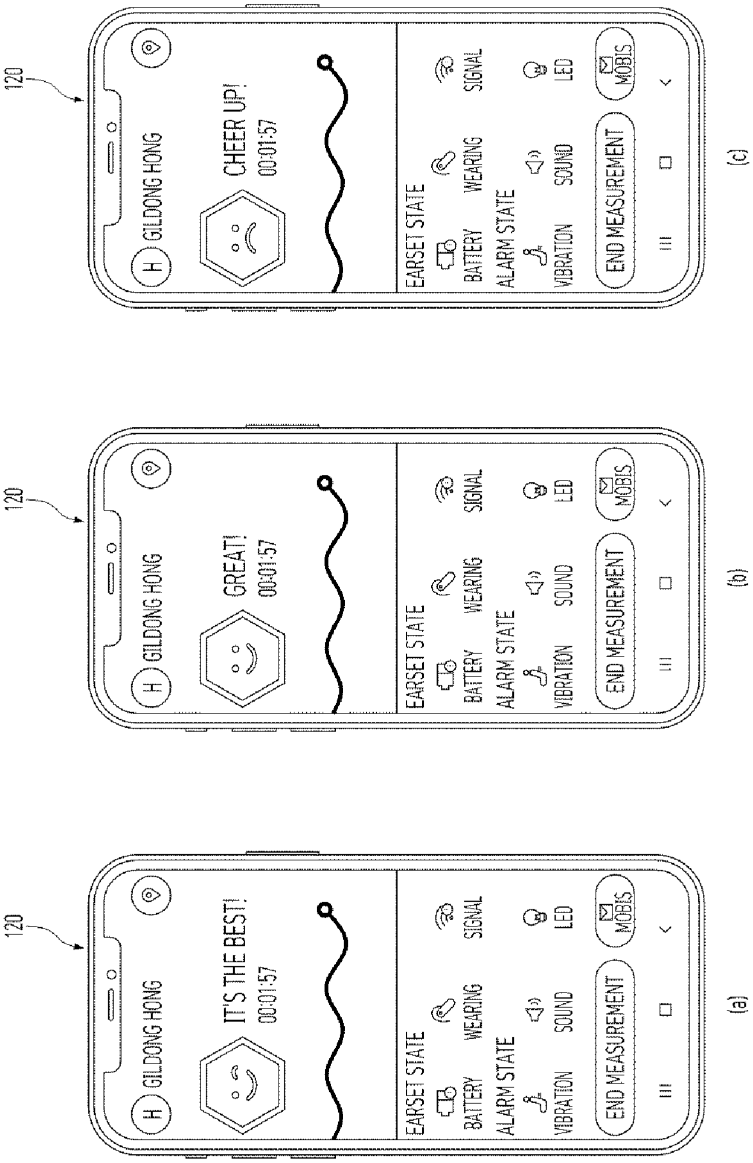
FIGS. 6 and 7 are diagrams showing various embodiments output via an app installed on a mobile terminal of a driver assistance system according to the present disclosure.
Figure 7:
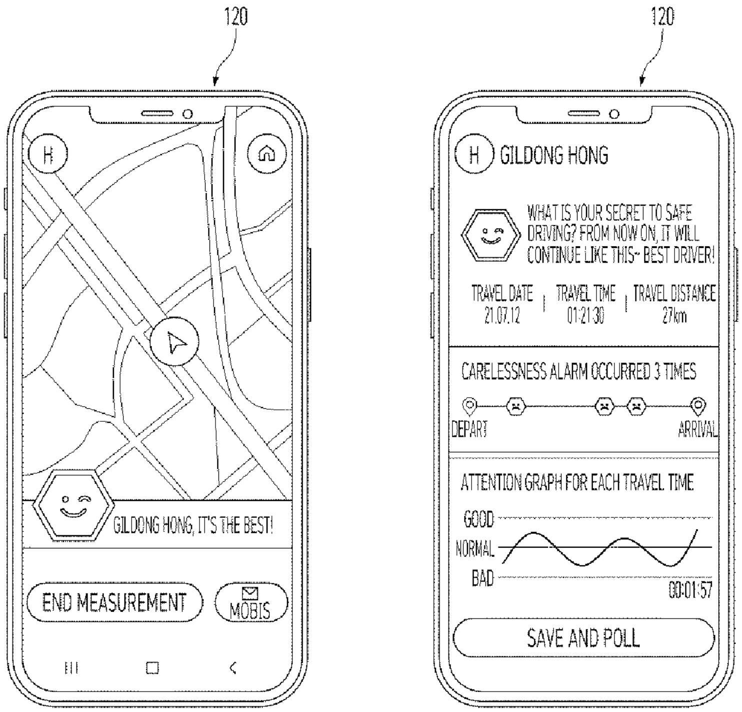

FIGS. 6 and 7 are diagrams showing various embodiments output via an app installed on the mobile terminal 120 of the driver assistance system 100 according to the present disclosure.

Referring to FIG. 1 together, in the driver assistance system 100 according to one embodiment of the present disclosure, the mobile terminal 120 may output the careless state of the driver via the app. In this regard, the mobile terminal 120 may output, via the app, at least one of an emoji, a text, a color, or the received electroencephalogram signal.

The careless state of the driver may be quantified via Mathematical Formula above, and the careless state of the driver may be determined via the comparison with the preset alertness value. In this regard, FIG. 6 is a diagram showing various embodiments of the app in which the determined careless state of the driver is output. As described above, (a) in FIG. 6 is a diagram showing a case in which the alertness of the driver is the best, (b) in FIG. 6 is a diagram showing a case in which the alertness of the driver is good, and (c) in FIG. 6 is a diagram showing a case in which the alertness of the driver is bad.

As shown in FIG. 6, the driver assistance system 100 according to one embodiment of the present disclosure may output the different emojis, texts, and colors based on the determined careless state of the driver via the app on the mobile terminal 120.

In addition, as described above with reference to FIG. 1, information on a wearing state of the earset and information on remaining battery power may also be output, and information on the alarm provided to the user may also be output by controlling the vehicle 140.

Additionally, in the driver assistance system 100 according to one embodiment of the present disclosure, the mobile terminal 120 may output a navigation screen or the number of alarms provided to the driver via the app. (a) in FIG. 7 is an example of a case of including the navigation screen, and (b) in FIG. 7 is a diagram showing an example of a case of including the number of alarms provided to the driver during a total travel time when the driver ends the driving and the analysis of the electroencephalogram signal is completed.

FIGS. 6 and 7 only show some of the embodiments output via the app installed on the mobile terminal 120 in the driver assistance system 100 according to the present disclosure. The information output via the app may be integrated, added, or omitted. That is, when necessary, two or more information may be combined into one information, or one information may be divided into two or more information and output.

Figure 8:
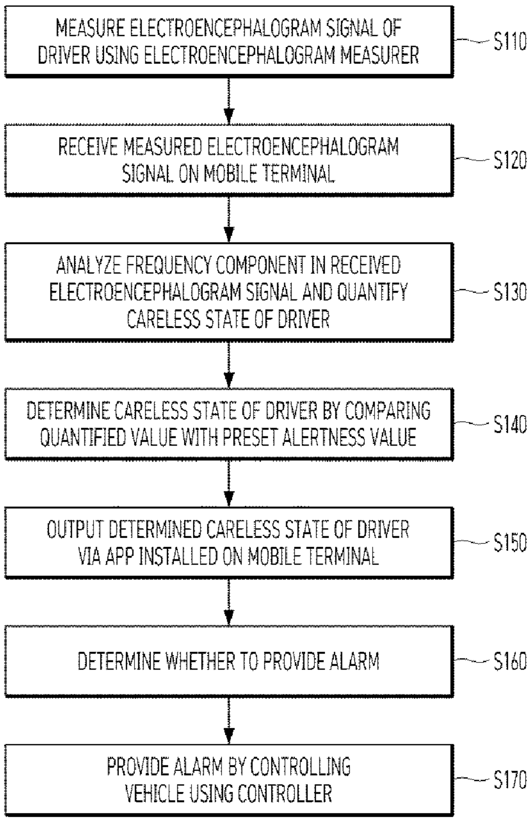
FIG. 8 is a diagram for illustrating a driver assistance method according to an embodiment of the present disclosure.

FIG. 8 is a diagram for illustrating a driver assistance method according to an embodiment of the present disclosure.

First, the electroencephalogram signal of the driver may be measured using the electroencephalogram measurer (S110). In addition, the measured electroencephalogram signal may be received on the mobile terminal (S120). In this regard, the driver assistance method according to one embodiment of the present disclosure may determine whether the driver is wearing the electroencephalogram measurer and, when the driver is not wearing the electroencephalogram measurer, generate the wearing recommendation signal to ask the driver to wear the electroencephalogram measurer. Such wearing recommendation signal may be generated periodically until the driver wears the electroencephalogram measurer. In addition, when the driver completes the driving, for example, when the transmission is placed in park, the removal recommendation signal to ask the driver to remove the electroencephalogram measurer may be generated when the driver does not remove the electroencephalogram measurer. Such removal recommendation signal may be generated periodically until the driver removes the electroencephalogram measurer. In addition, the wearing recommendation signal and the removal recommendation signal may be output via the outputter of the mobile terminal such that the driver may recognize those.

The driver assistance method according to one embodiment of the present disclosure may analyze the frequency component in the electroencephalogram signal received from the electroencephalogram measurer and quantify the careless state of the driver using the analyzed frequency component (S130). In addition, the careless state of the driver may be determined by comparing the quantified value with the preset alertness value (S140).

In this regard, the determining of the careless state of the driver may include analyzing the frequency component via the window size in the first time unit in the received electroencephalogram signal. Additionally, shifting the window size into the second time unit on the time axis and analyzing the frequency component as much as the window size may be included.

In this regard, as mentioned above, one embodiment of the present disclosure may calculate the average value of the theta, beta, and SMR frequency intensities for 4 seconds from the electroencephalogram signal every second via the 4-second window size and the 1-second shift, and quantify the careless state of the driver via Mathematical Formula above.

In this regard, the analyzing of the frequency component may include classifying the frequency component by performing the Fourier transform on the received electroencephalogram signal, and the classified frequency component may include at least one of the theta, beta, or SMR frequencies. In addition, the careless state of the driver may be quantified using the classified frequency component.

As described above, the Fourier transform may be the concept that includes all of the Fast Fourier Transform (FFT), the Short Time Fourier Transform (STFT), and the like. In addition, the careless state of the driver may be quantified as the value from 0 to 100 via Mathematical Formula above.

In this regard, the preset alertness value may be set, for example, by classifying the range equal to or lower than 55 into the range with the poor alertness, the range from 56 to 80 into the range with the good alertness, and the range from 81 to 100 into the range with the highest alertness. Therefore, according to the above example, when the value quantified via Mathematical Formula above is 50, this corresponds to the section where the alertness is poor compared to the preset alertness value, which may be determined as the careless state of the driver.

Thereafter, the determined careless state of the driver may be output via the app installed on the mobile terminal (S150). In addition, whether to provide the alarm to the driver may be determined considering whether the driver is in the carelessness state (S160), and the vehicle may be controlled via the controller to provide the alarm to the driver (S170).

Figure 9:
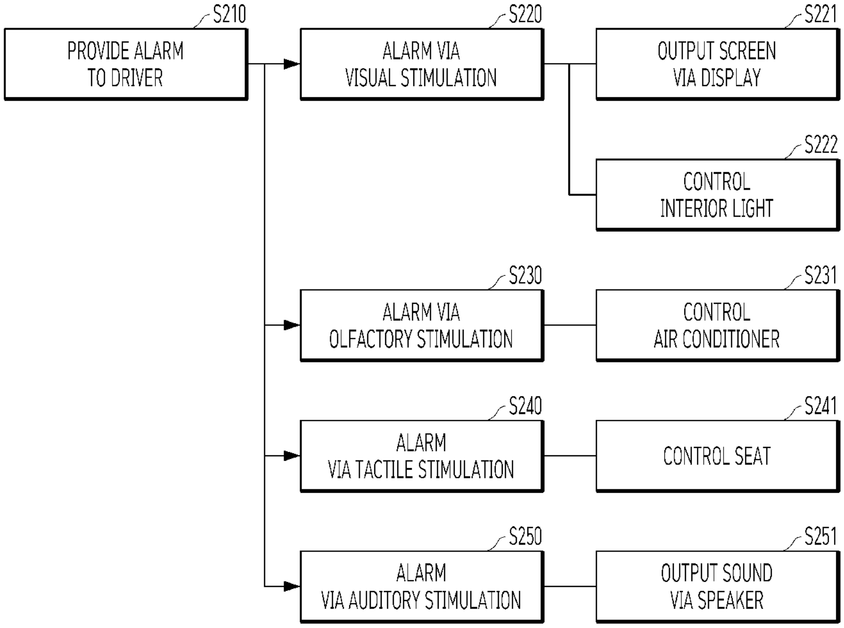
FIG. 9 is a diagram showing various embodiments that provide an alarm to a driver in a driver assistance method according to the present disclosure.

FIG. 9 is a diagram showing various embodiments that provide an alarm to a driver in a driver assistance method according to the present disclosure.

The present disclosure may provide the alarm to the driver in various ways (S210), and in particular, the alarm may be provided to the driver via the various stimuli.

The alarm via the visual stimulation may be provided (S220), which may include outputting the screen via the display (S221) or controlling the interior light (S222). In this regard, the interior light may be the mood light or the ambient light inside the vehicle. Additionally, the interior light may include the LED installed above the cluster fascia of the driver's seat or installed on the side surface of the seat. In addition, the alarm may be provided to the driver via the visual stimulation by controlling ON and OFF of the LED power.

Additionally, the alarm via the olfactory stimulation may be provided (S230), which may include controlling the air conditioner (S231) to control the indoor temperature or introducing the external air. For example, the controller may control the indoor temperature by operating the air conditioner to lower the indoor temperature when the concentration of the driver decreases. To lower the carbon dioxide concentration, the external air may be controlled to flow into the vehicle 140 in the external air circulation mode, and the air conditioner may be controlled to generate the olfactory stimulation to the driver using the air freshener and the like.

Additionally, the alarm via the tactile stimulation may be provided (S240), which may include controlling the seat (S241). For example, the alarm may be provided to the driver via the tactile stimulation, including controlling the massage device installed in the seat or controlling the ventilation device or the adjustable device.

Additionally, the alarm via the auditory stimulation may be provided (S250), which may include outputting the sound via the speaker (S251). In one embodiment, the speaker may be located on the headrest of the seat and provide the alarm to the driver via the auditory stimulation at the location close to both ears of the driver.

Figure 10:
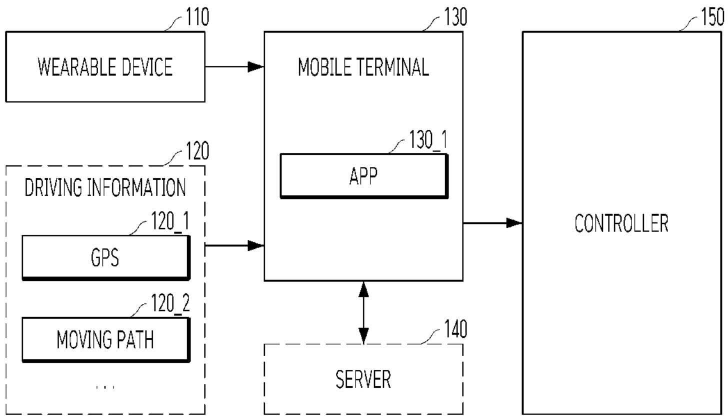
FIG. 10 is a diagram for illustrating a configuration of a driver assistance system according to an embodiment of the present disclosure.

FIG. 10 is a diagram for illustrating a configuration of a driver assistance system according to an embodiment of the present disclosure.

The driver assistance system using the electroencephalogram shown in FIG. 10 includes a wearable device 110 that measures the electroencephalogram signal of the driver, and a mobile terminal 130 equipped with an app 130_1 that receives the electroencephalogram signal measured by the wearable device 110, processes the received electroencephalogram signal and provides the processed signal to a server 140, and receives carelessness alarm information converted into big data from the server 140.

Additionally, the driver assistance system according to the present embodiment may include a controller 150 that controls a mobility based on the carelessness alarm information received from the server 140 and provides a carelessness-related alarm to the driver.

The above-described driver assistance system may operate using various driving information acquisitors 120 and the server 140 equipped in the mobility as shown in FIG. 10, in addition to the wearable device 110, the mobile terminal 130, and the controller 150. However, the components such as the driving information acquisitor 120 and the server 140 are components of an existing mobility and may not be included in the driver assistance system according to the present embodiment.

As shown in FIG. 10, the mobile terminal 130 according to the present embodiment may not only receive the electroencephalogram signal from the wearable device 110 and utilize the signal, but also acquire various driving information signals from the driving information acquisitor 120 and utilize the signals. The driving information signal may include at least one of a GPS signal 120_1, a moving path signal 120_2 of the mobility, a time information signal, and a weather information signal. Such information may be acquired from components already disposed in the mobility, or the time information, the weather information, and the like. may be acquired by the mobile terminal 130 itself.

It is proposed that, rather than collecting and processing such information to generate the carelessness alarm information on its own, the app 130_1 of the mobile terminal 130 according to the present embodiment utilizes the carelessness alarm information based on the information converted into the big data via the server 140. In other words, the server 140 may provide more accurate and diverse alarm information by utilizing the driving information corresponding to a plurality of mobilities and the electroencephalogram information corresponding to the driving information.

Figure 11:
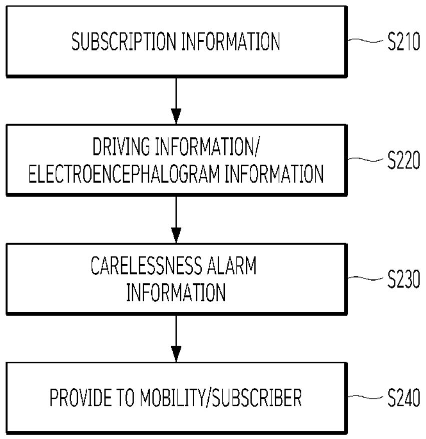
FIG. 11 is a diagram for illustrating a method for providing a driver assistance service based on an electroencephalogram of a server according to an embodiment of the present disclosure.

FIG. 11 is a diagram for illustrating a method for providing a driver assistance service based on an electroencephalogram of a server according to an embodiment of the present disclosure.

The electroencephalogram-based driver assistance service providing method shown in FIG. 11 is an example for providing an assistance service to a bus driver and shows a method performed at an end of the server 140 in FIG. 10.

First, the server 140 may acquire subscription information of the drivers of the plurality of mobilities (S210). As an example of the subscription information of the driver, subscription information of a bus driver may include information for a bus transportation company to subscribe the present driver assistance service and subscription information of an individual driver.

Next, when the plurality of mobilities are in travel, the server 140 may receive the driving information and the electroencephalogram signal information of the respective drivers of the plurality of mobilities (S220). As described above, the driving information may include the GPS information and moving path information (e.g., bus line information, current operation state information, and the like), and the electroencephalogram information for each moving path may be received. The electroencephalogram information received from the server 140 may be electroencephalogram information processed for each individual driver in the app 130_1 of the mobile terminal 130, and the processing of the electroencephalogram signal for each individual driver will be described in detail below.

The server 140 according to the present embodiment may generate the carelessness alarm information converted into the big data based on the driving information and the electroencephalogram signal information received as described above (S230), and provide the carelessness alarm information generated as such to the plurality of mobilities or the subscribers (S240).

The carelessness alarm information may include at least one of information on in which moving path or location the carelessness occurs, information on in what time period the carelessness occurs, and information on under what weather the carelessness occurs. Rather than being generated at a level of the individual mobile terminal 130 or mobility, such information is generated at the end of the server 140 based on information on the plurality of mobilities, thereby ensuring the objectivity and providing the alarm on the carelessness in more diverse aspects.

Figure 12:
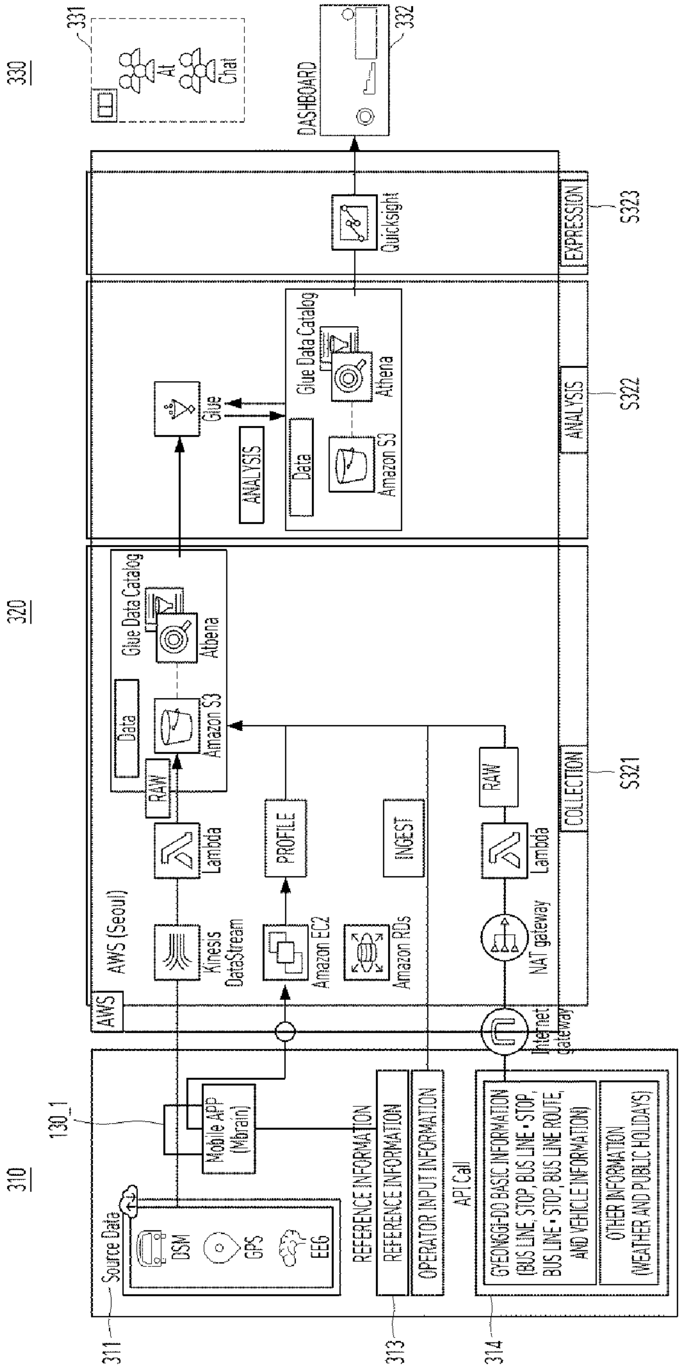
FIG. 12 is a diagram showing an example configuration of an entire driver assistance system including a server according to an embodiment of the present disclosure.

FIG. 12 is a diagram showing an example configuration of an entire driver assistance system including a server according to an embodiment of the present disclosure.

First, in the example of configuration of the system shown in FIG. 12, components are expressed as being divided into an information collection end 310, a server end 320, and a user end 330.

The information collection end 310 may include deep learning-based driver state monitoring (DSM) information, GPS information, and electroencephalogram (EEG) information as source data 311.

In addition, the information collection end 310 may include information acquired via the app 130_1, which may include driver information of the bus company and input information 313 of each driver. However, the driver information of the bus company and the input information 313 of each driver do not necessarily need to be input via the app 130_1 of the mobile terminal 130, and the app 130_1 is able to be installed on various computing devices to provide corresponding reference information.

In addition, the information collection end 310 may include means 314 for acquiring base information (e.g., Gyeonggi-do bus line information, bus line stop information, and vehicle information), weather information, and the like in a corresponding area in addition to the above-described information.

At the server end 320, as described above, the method may be largely divided into collecting the various information from the information collection end 310 (S321), analyzing the information collected as such (S322), and expressing and providing the alarm information to the user or a computing device of the bus company using the analyzed result (S323). FIG. 12 shows an example of performing deep learning-based big data conversion of a specific cloud service, but the present embodiment does not need to be limited to such specific cloud service.

The user end 330 may include individual drivers 331 and a computing device dashboard of a bus company 332, as shown in FIG. 12. In the present embodiment, the carelessness alarm based on the electroencephalogram-based analysis result may be provided to the individual drivers 331 via various components (e.g., an alarm, a vibration, a display, a sound, and the like) of the mobility. In addition, statistics such as which section of which line the carelessness occurs, carelessness of which driver is frequent, and the like may be provided via the computing device dashboard of the bus company 332.

FIGS. 13 to 16 are diagrams for illustrating a method for acquiring and managing subscriber information according to an embodiment of the present disclosure.

Figure 13:
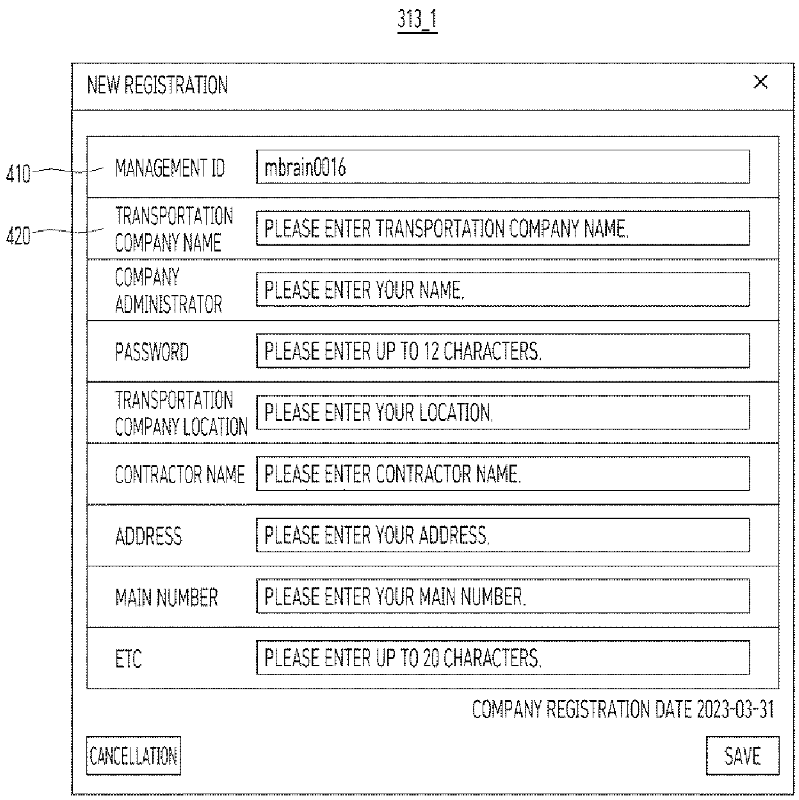
FIGS. 13, 14, 15, and 16 are diagrams for illustrating a method for acquiring and managing subscriber information according to an embodiment of the present disclosure.
Figure 15:
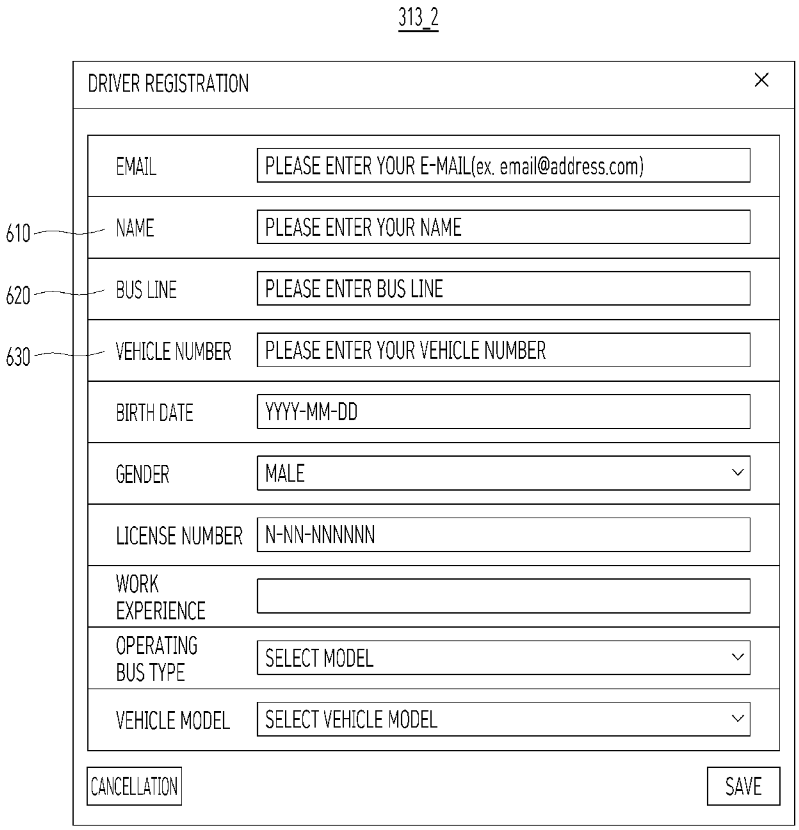

As described above, the subscriber information may be divided into subscription information 313_1 of each transportation company, such as the bus company, and input information 313_2 of each driver. FIG. 13 shows an example of the subscription information 313_1 of each transportation company, and FIG. 15 shows an example of the input information 313_2 of each driver.

As shown in FIG. 13, in the subscription information 313_1 of each transport company, each transport company name 410 and information necessary for management may be input. As each transport company name 410, a management ID 410 on the system according to the present embodiment may be assigned and managed.

Figure 14:
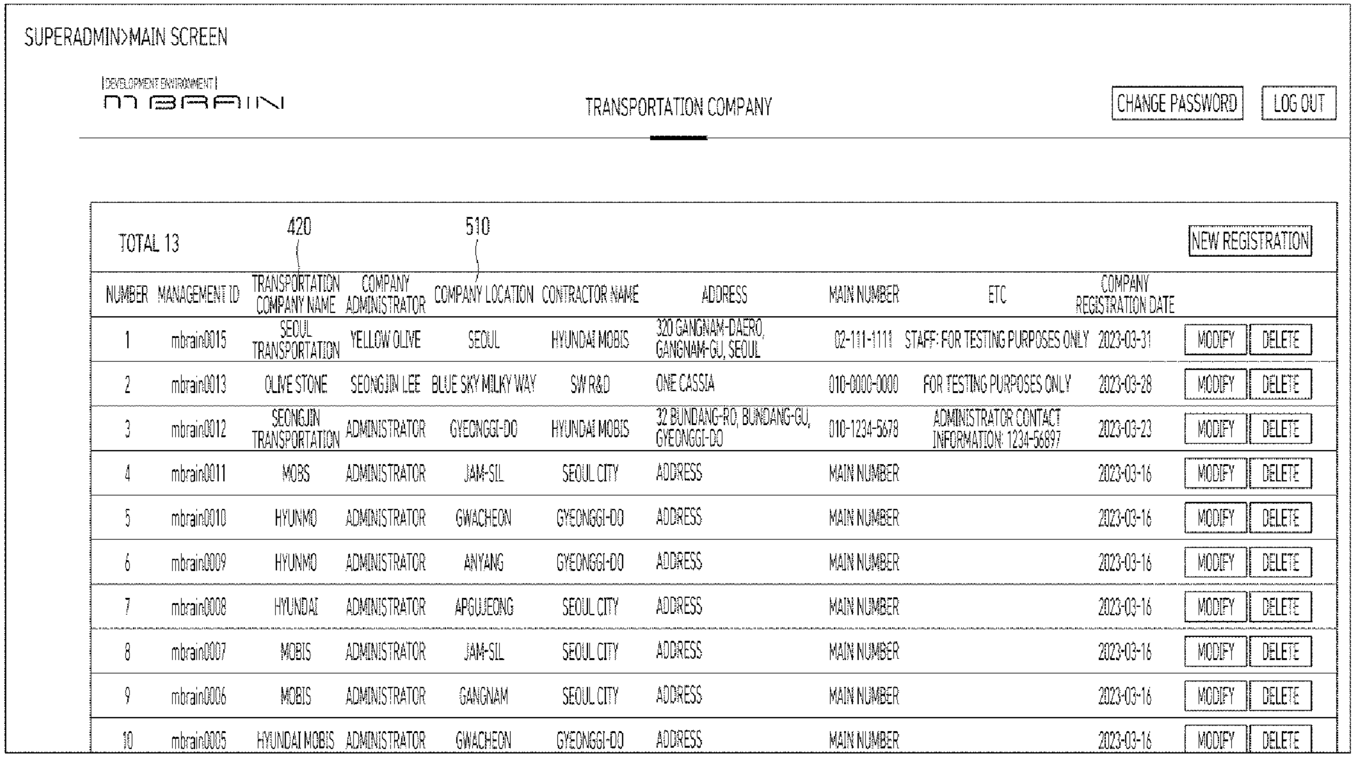

FIG. 14 shows an example of an administrator screen 500 displayed based on the subscription information 313_1 input for each transportation company, as shown in FIG. 13.

Information necessary for the administrator may be displayed as shown in FIG. 14 for each transportation company name 420 input in FIG. 13. In this regard, area information 510 of a corresponding transportation company may be managed for each transportation company name 420, and driving assistance information such as line information of the corresponding area may be coupled and analyzed based on the area information 510.

As shown in FIG. 15, as the input information 313_2 of each driver, a name 610 of each driver, an operating bus line 620, a vehicle number 630, and other necessary information may be input.

Figure 16:
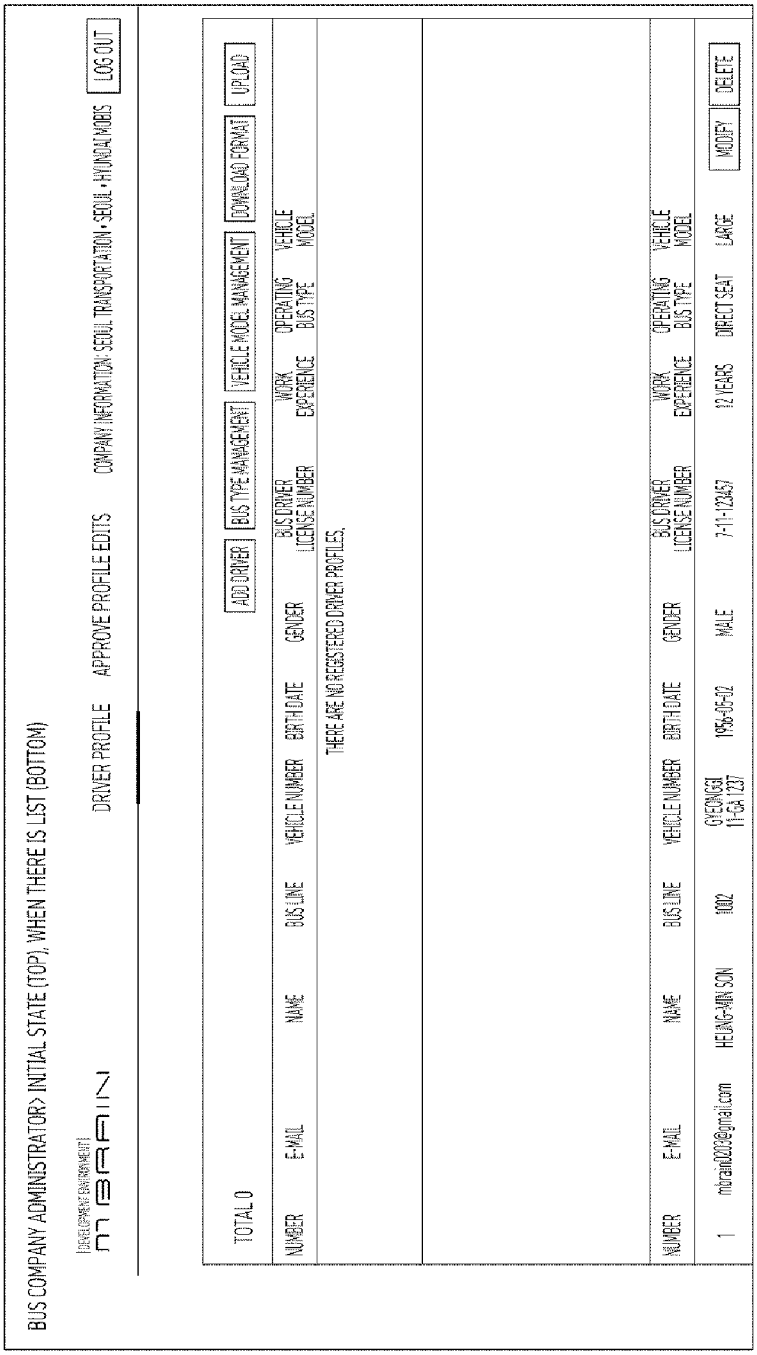

The driver information input as such may be displayed on an administrator screen 700 as shown in FIG. 16. Top of FIG. 16 indicates a state in which the corresponding driver is not registered, and bottom of FIG. 16 indicates a state in which the corresponding driver is registered and displayed.

A carelessness occurring section/frequency may be calculated for each line via the information such as the operating bus line 620 and the vehicle number 630 among the input information 313_2 of each driver described above. Additionally, statistics on a degree of carelessness based on an age/gender of the driver may be provided using additional personal information of the input information 313_2 of each driver.

FIGS. 17 to 20 are diagrams showing examples of carelessness alarm information according to various embodiments of the present disclosure.

Figure 17:
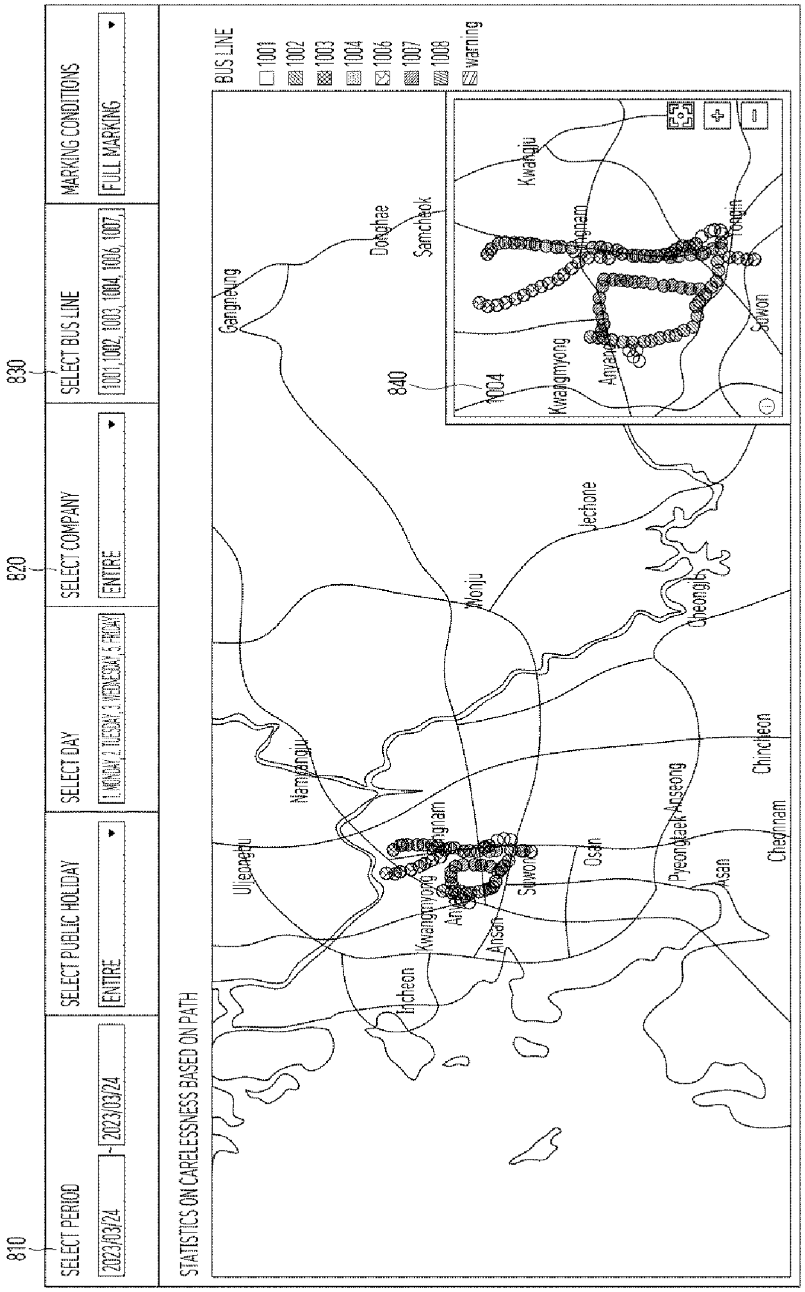
FIGS. 17, 18, 19, and 20 are diagrams showing examples of carelessness alarm information according to various embodiments of the present disclosure.

First, FIG. 17 shows an example of displaying information on a section where the carelessness has occurred for each line in a specific time period. In terms of selection of the time period, as shown in FIG. 17, a date range 810 may be selected, or statistics for a public holiday or each day of the week may be selected. A displayed screen may be selected for each transportation company 820 or for each line 830. As shown in FIG. 17, as the line, a plurality of lines operating in the corresponding area may be selected simultaneously to identify a trend of the carelessness occurrence in each area.

To examine a specific line in detail while displaying carelessness sections in a form of a map for the plurality of lines, the specific line may be selected and carelessness section information of the corresponding line may be displayed in an enlarged manner (840).

Figure 18:
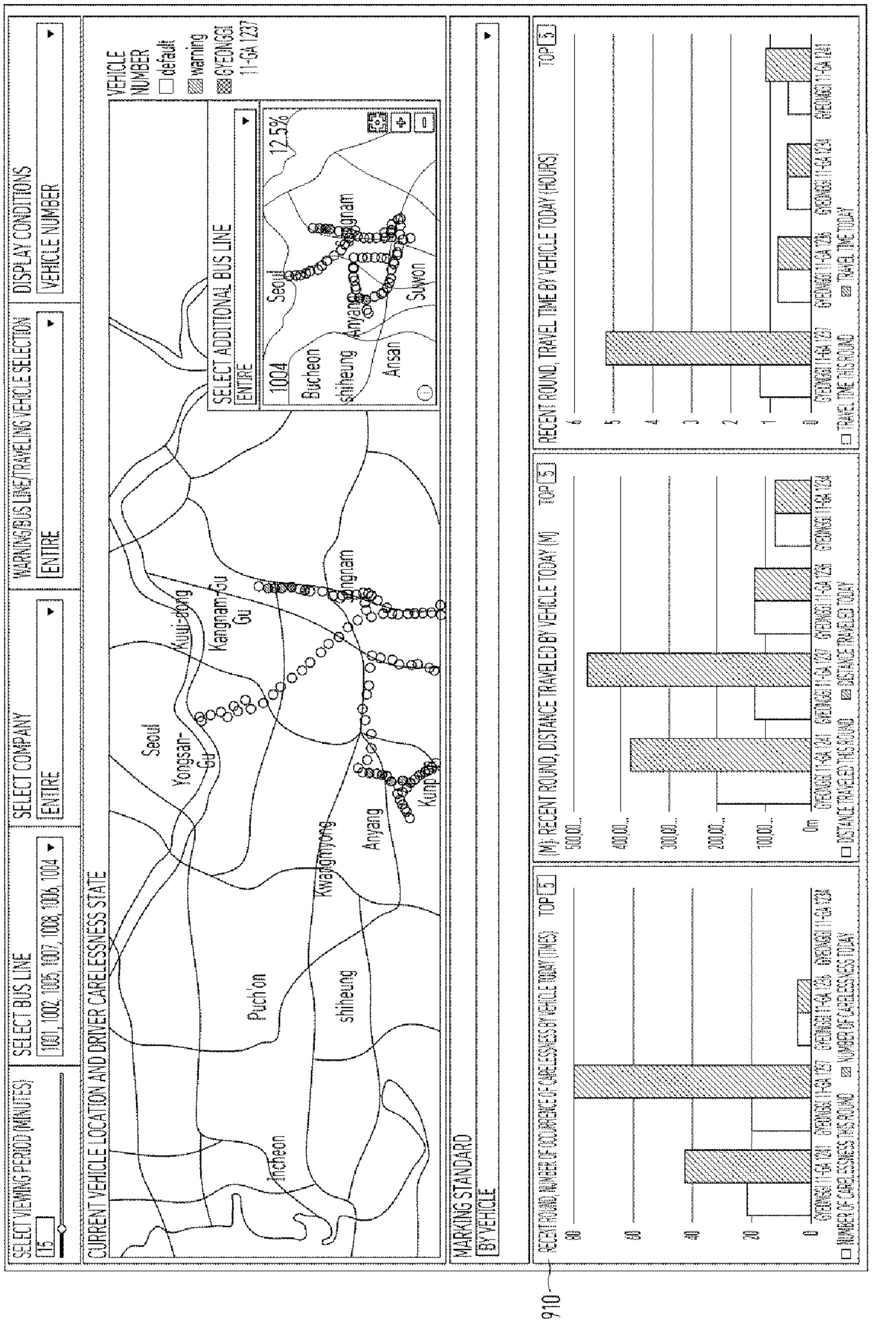

FIG. 18 shows an example of additionally displaying statistics 910 on the number of carelessness alarms in a specific time period on a screen displayed as in FIG. 17. The statistics 910 on the number of carelessness alarms may be displayed for each vehicle of the corresponding line, as illustrated in FIG. 18, or alternatively, may be displayed for each bus line.

Figure 19:
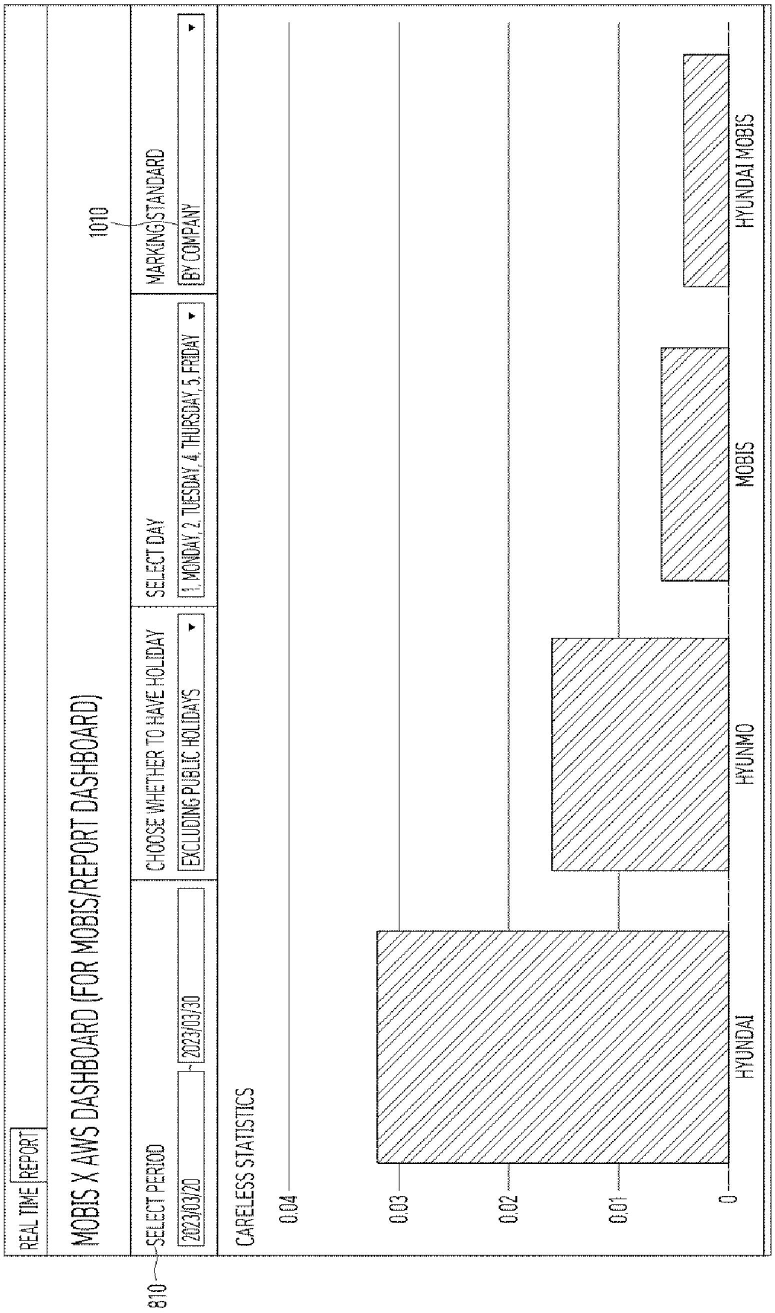
Figure 20:
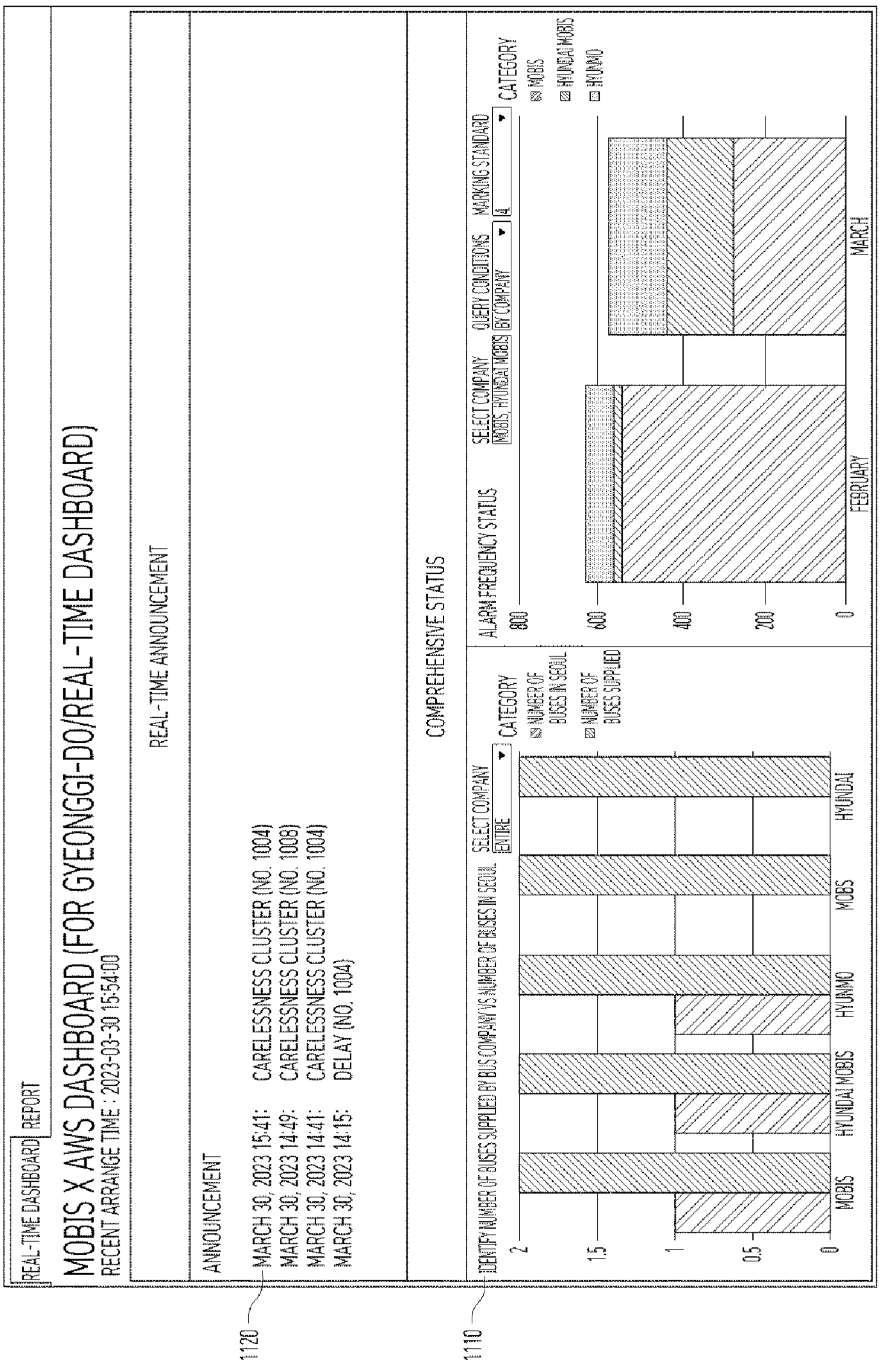

FIG. 19 is a diagram showing statistics on an occurrence of carelessness alarms for each company 1010 in a specific time period 810, and FIG. 20 shows examples of a screen to display information on a carelessness cluster for each company 1110 and for each time 1120 as information that may be provided to a local organization (e.g., Gyeonggi-do) of the corresponding area. That is, the carelessness alarm information according to one embodiment of the present disclosure may include alarm information provided for each driver, alarm information provided for each transportation company, alarm information provided for each local organization, and the like.

The carelessness alarm information as described above are illustrative, and depending on embodiments of the present disclosure, the carelessness alarm information is able to include various information as shown in <Table 1> below.

TABLE 1

| |
|---|
| Which bus line does carelessness occur often? |
| Which bus vehicle does carelessness occur often? |
| At what stop does carelessness occur often? |
| With which bus driver and in which area does carelessness occur often? |
| In which area, including city/rural area, does carelessness occur often? |
| In what year/month/day does carelessness occur often? |
| Does carelessness occur more often on weekdays or weekends? |
| At what time of day does carelessness occur often? |
| In what weather does carelessness occur often? |

Figure 21:
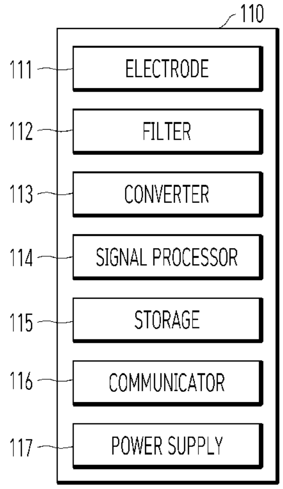
FIGS. 21 and 22 are diagrams for illustrating a configuration of a wearable device according to embodiments of the present disclosure.
Figure 22:
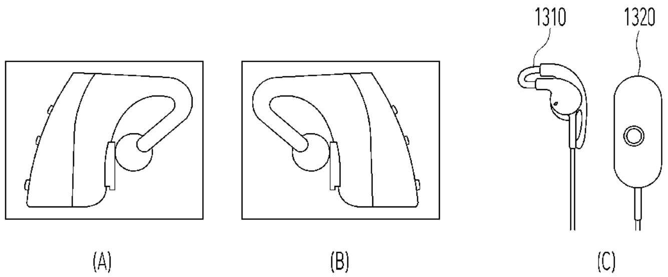

FIGS. 21 and 22 are diagrams for illustrating a configuration of a wearable device according to embodiments of the present disclosure.

The driver assistance system according to one embodiment of the present disclosure may measure the electroencephalogram signal of the driver via the wearable device 110. The electroencephalogram (EEG) is the phenomenon in which the thoughts, the emotions, and the behaviors of the individual are generated by the communication between the nerve cells in the brain, and is the synchronized electrical wave generated when the nerve cells in the cerebral cortex transmit the signals to each other. As described above, the electroencephalogram appears in the various frequency bands, and is able to be specifically classified into the delta wave, the theta wave, the alpha wave, the beta wave, the gamma wave, and the like based on the frequency bands.

In this regard, the wearable device 110 may include the earset that is mounted around the ear of the driver and is able to measure the electroencephalogram signal around the left or right temporal lobe of the driver while driving. In another embodiment, the wearable device 110 may include the headset using the multi-channel electrode.

In addition, in the driver assistance system 100 according to one embodiment of the present disclosure, the wearable device 110 may include the various sensors or equipment that may measure the electroencephalogram signal of the driver in real time, including the earset and the headset described above.

The electrode 111 may measure the electroencephalogram signal of the driver during the driving and/or the stopping of the driver in the vehicle 140 via the electrode. In this regard, the electrode 111 may include the EEG electrode, the REF electrode, and the GND electrode. The EEG electrode is the conductive electroencephalogram electrode, and is able to measure the electroencephalogram signal of the left or right temporal lobe by being in contact with the area near the left or right temporal lobe temple of the driver. The REF electrode is the reference electrode, and is able to provide the reference potential when the EEG electrode measures the electroencephalogram signal. The GND electrode is the ground electrode, is located on the back of the earflap, and is able to serve as the ground when the EEG electrode measures the electroencephalogram signal.

In one embodiment, the filter 112 may remove the noise from the electroencephalogram signal of the driver measured by the electrode 111. The filter 112 may remove the noise from the electroencephalogram signal using the high pass filter, the low pass filter, or the band pass filter. As another embodiment, the filter such as the notch filter or the active filter may be used. In this regard, the noise may include the noise generated by the eye-blink of the driver, the AC power noise, and the DC drift component as well as all the elements that interfere with the feature point extraction.

The converter 113 may convert the noise-removed electroencephalogram signal of the driver into the digital signal. The signal processor 114 may calculate one or more characteristics of the electroencephalogram from the electroencephalogram signal of the driver measured by the wearable device 110. The characteristics of the electroencephalogram calculated by the signal processor 114 may be, for example, at least one of the magnitude of the electroencephalogram signal in the time domain, the magnitude of the electroencephalogram signal in the frequency domain, and the magnitude of the signal-to-noise ratio (SNR) peak.

The storage 115 may store the reference electroencephalogram signal, that is, the preset alertness value, for determining the careless state of the driver based on the characteristics of the electroencephalogram. In this regard, the careless state of the driver may include the state in which the driver is not able to concentrate on the driving, including the abnormal states such as the drowsiness, the reduced concentration, and the surprise. In addition, the storage 115 may store the electroencephalogram signal of the driver measured via the wearable device 110 for a certain period of time. Such storage 115 may include the internal memory and/or the external memory, and may include the volatile memory such as the DRAM, the SRAM, or the SDRAM, the non-volatile memory such as the one time programmable ROM (OTPROM), the PROM, the EPROM, the EEPROM, the mask ROM, the flash ROM, the NAND flash memory, or the NOR flash memory, and the storage device such as the SSD, the compact flash (CF) card, the SD card, the micro-SD card, the mini-SD card, the XD card, the flash drive such as the memory stick, or the HDD.

The communicator 116 is the medium for transmitting and receiving the information between the wearable device 110 and the mobile terminal or the vehicle, and is able to transmit the electroencephalogram signal of the driver measured by the wearable device 110 to the mobile terminal or the vehicle via the wireless communication. In the present embodiment, the communicator 116 may transmit and receive the data with the mobile terminal or the vehicle via at least one communication among the Bluetooth, the radio frequency identification (RFID), the infrared data association (IrDA), the ultra-wideband (UWB), the ZigBee, and the wireless fidelity (Wi-Fi) technologies.

The power supply 117 may supply the corresponding power throughout the wearable device 110. Specifically, the power supply 117 may include the converter that converts the AC power to the DC power and the DC/Dc converter that converts the level of the DC power. The power supply 117 may use the scheme of supplying the AC power via the direct connection to the external power source, and may include the power supply 117 that includes the battery to be charged and used.

In the case of the former, the cable is connected to the power supply 117, so that it is difficult for the power supply 117 to move or the range of movement thereof is limited. In the case of the latter, the power supply 117 is free to move, but the weight and the volume thereof increase as much as those of the battery, and the power supply 117 must be directly connected to the power cable or coupled to the charging holder that supplies power for a certain period of time for the charging. The charging holder may be connected to the wearable device 110 via the terminal thereof exposed to the outside, or the built-in battery may be charged when approaching the charging holder using the wireless scheme.

FIG. 22 illustrates three types of wearable device 110 according to embodiments of the present disclosure.

First, (A) in FIG. 22 shows an example that may be worn on a right ear of the driver, and (B) in FIG. 22 shows an example that may be worn on a left ear of the driver.

In a case of a bus driver in a country where the driver's seat is generally located on a left side, such as Korea, when the driver is wearing the wearable device 110 for measuring the electroencephalogram on the right ear as shown in (A) in FIG. 22, there may be a difficulty recognizing a situation in which a passenger approaches and talks. Therefore, in the country such as Korea where the driver's seat is located on the left side, the wearable device 110 that may be worn on the left ear of the user, as shown in (B) in FIG. 22, may be more advantageous.

However, the above description applies to the country where the driver's seat is located on the left side, such as Korea. On the other hand, in countries where the driver's seat is located on a right side, such as Japan/England, the wearable device that is worn on the right ear of the driver as shown in (A) in FIG. 22 may be more advantageous.

On the other hand, the wearable device 110 according to the embodiment shown in (A) and (B) in FIG. 22 may include all of the components described above in FIG. 21, so that the wearable device 110 may be heavy and uncomfortable for the drivers.

Therefore, in a preferred embodiment of the present disclosure, as shown in (C) in FIG. 22, a measurer 1310 that may be worn on the ear of the driver and a functional member 1320 including a battery that supplies power to the measurer 1310 are separated from each other. It is proposed that the functional member 1320 may be fixed to another body part other than the ear of the driver or a fixture.

In other words, the functional member 1320 is constructed to include a component that is heavy and does not necessarily need to be in contact with the driver among the components of the wearable device 110, and to be fixed to clothes of the driver in a form of a clip, thereby reducing the weight of the wearable device 110 while maintaining high performance of the wearable device 110.

For example, the measurer 1310 may be constructed to include the electrode 111, the filter 112, the converter 113, and the signal processor 114 among the components described above in FIG. 21, and the functional member 1320 may be constructed to include the storage 115, the communicator 116, and the power supply 117. However, such separated arrangement of the components may be made in a different way by comparing an advantage of being connected to the driver's body and an advantage of reducing the weight with each other.

Figure 23:
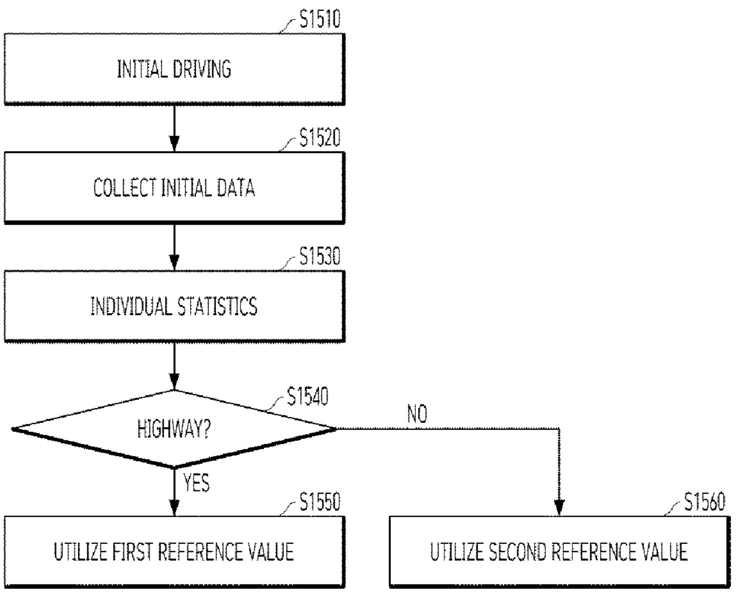
FIGS. 23 and 24 are diagrams for illustrating a method for processing and utilizing an electroencephalogram signal according to an embodiment of the present disclosure.
Figure 24:
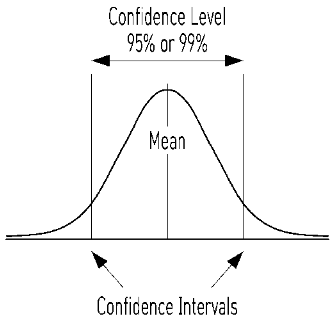

FIGS. 23 and 24 are diagrams for illustrating a method for processing and utilizing an electroencephalogram signal according to an embodiment of the present disclosure.

For measuring the electroencephalogram signal of the driver via the wearable device 110, measuring the electroencephalogram of the driver for each waveform (e.g., theta, SMR, and mid-beta in frequency ranges indicated at top of FIG. 24) on the same standard and quantifying the measurement results may be considered, but this may not take into account the differences in the electroencephalogram signals depending on the alertness between the drivers. Therefore, in a preferred embodiment of the present disclosure, it is proposed to consider the electroencephalogram characteristics of each driver and determine a degree of carelessness based on the characteristics.

To this end, in the embodiment shown in FIG. 23, first, the electroencephalogram signal may be measured during a predetermined time period while the driver wears the wearable device 110 and drives (S1510).

The predetermined time period is a time period for extracting the electroencephalogram characteristics for each driver using the electroencephalogram during initial travel of the driver, and is assumed to be set to 5 minutes. After collecting electroencephalogram data of the driver for the first 5 minutes as such (S1520), statistics on carelessness numeric values of the corresponding individual driver may be calculated based on the collected data (S1530). For example, such statistics on the carelessness numeric values of each individual may be calculated as a distribution as shown at bottom of FIG. 24. Mean ($\mu$) and standard deviation ($\sigma$) may be calculated from the distribution, and may be recorded/saved. In this regard, it may be efficient to measure the electroencephalogram signal by excluding an alertness score with a deviation equal to or greater than $3\sigma$ as an outlier.

When the degree of carelessness of each driver is determined using the mean (μ) and the standard deviation (σ) as described above, an alarm may be provided on the degree of carelessness of the corresponding driver in consideration of individual characteristics of the driver.

In the preferred embodiment of the present disclosure, it is proposed to additionally consider a travel state in determining the degree of carelessness of the driver. As an example, in FIG. 23, it is proposed to provide the carelessness alarm based on different standards by determining whether the corresponding mobility is travelling on a highway (S1540). Whether the mobility is traveling on the highway may be determined by whether the corresponding mobility maintains a travel at a speed equal to or higher than 60 km/h for 10 seconds.

When the corresponding mobility is traveling on the highway, whether to provide the carelessness alarm may be determined based on a first reference value (S1550). For example, when the mobility is traveling on the highway, and when the alertness score is equal to or smaller than $\mu-1.96\sigma$ (the first reference value), it may be set to provide the carelessness alarm to the corresponding driver, which may correspond to a 95% confidence interval in the distribution shown at the bottom of FIG. 24.

On the other hand, when the mobility is traveling on a general road, and when the alertness score is equal to or smaller than $\mu-2.58\sigma$ (a second reference value), it may be set to provide the carelessness alarm to the corresponding driver, which may correspond to 99% confidence interval in the distribution shown at the bottom of FIG. 24. In other words, in the present embodiment, it is proposed to prevent major accidents in advance by providing the carelessness alarm using a standard higher than that in the case of traveling on the highway.

In the above-described embodiment, it is desirable to set the carelessness alarm not to be provided for 5 minutes set to identify the electroencephalogram characteristics of each driver at start of each travel. Additionally, when the driver is not properly wearing the wearable device, a separate alarm may be provided, but it is desirable to set the carelessness alarm not to be activated in such situation.

Although the example of recording/saving the electroencephalogram characteristics of the specific driver for 5 minutes after the start of travel is illustrated in the above-described embodiment, the electroencephalogram characteristics of the driver may also be used in a scheme of being managed by the server by calculating the mean and the standard deviation in a 24-hour period.

Figure 25:
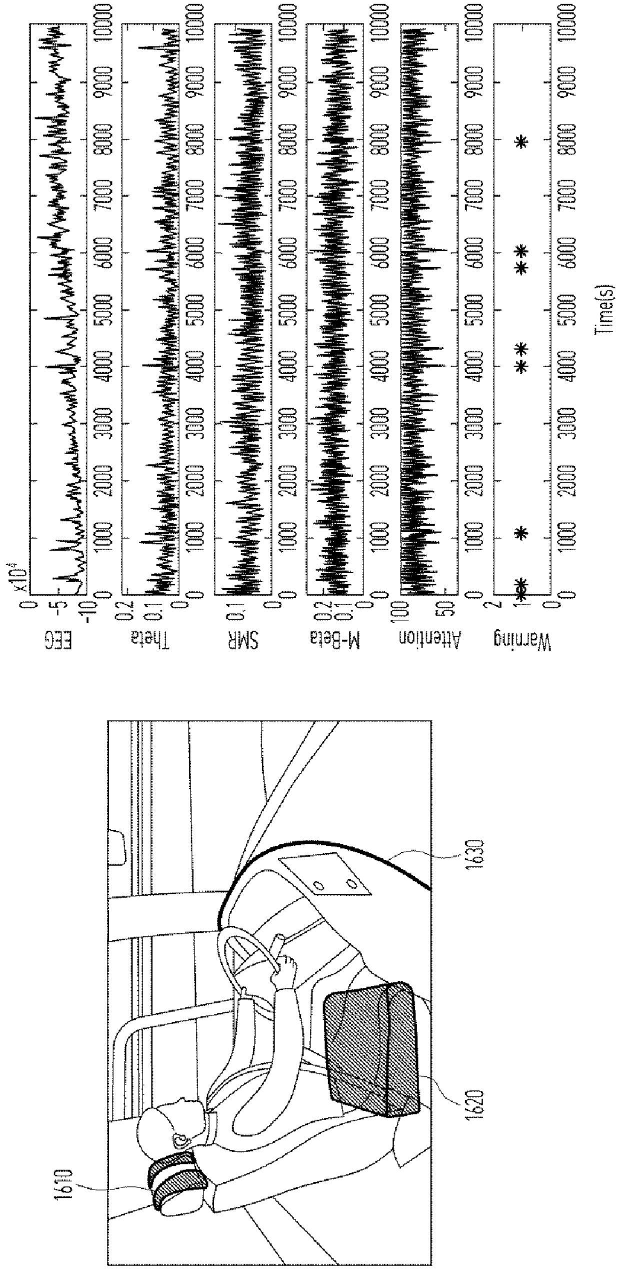
FIG. 25 is a diagram for illustrating a concept of providing a carelessness alarm to a driver according to an embodiment of the present disclosure.

FIG. 25 is a diagram for illustrating a concept of providing a carelessness alarm to a driver according to an embodiment of the present disclosure.

On a left side of FIG. 25, a method for providing sound via a speaker 1610 located on the headrest, a method for providing vibration and/or ventilation via a lower end 1620 of the driver's seat, and a method for providing the carelessness alarm via lighting of a light 1630 such as the LED disposed in front of the driver's seat are illustrated as an example as the method for providing the carelessness alarm to the driver.

On the other hand, a right side of FIG. 25 shows various electroencephalograms measured via the wearable device 110 worn by the driver. In other words, the electroencephalogram measured from the driver may not be limited to the theta, the SMR, and the mid-beta indicated at the top of FIG. 24, and the various electroencephalograms may be measured.

In addition, in the above-described embodiments of the present disclosure, the description has been made centering on the method for providing the carelessness alarm to the driver based on the electroencephalogram, but in another embodiment of the present disclosure, such an electroencephalogram-based carelessness alarm method and an image-based carelessness alarm method may be used in combination with each other.

The electroencephalogram-based carelessness alarm method has an advantage of being able to quickly determine the careless state of the driver and provide the alarm compared to the image-based carelessness alarm method. For example, the image-based carelessness alarm method may provide the alarm related to the carelessness of the driver via a change in an image of driver's actual eyelids closing when the driver is drowsy, whereas the electroencephalogram-based carelessness alarm method has an advantage of providing the alarm for the carelessness situation via the electroencephalogram of the driver before the actual eyelids are closed.

However, in a situation where the driver is not drowsy and has concentration, but is not looking forward, the image-based carelessness alarm method may have an advantage over the electroencephalogram-based carelessness alarm method. Therefore, in the embodiment of the present disclosure, it may also be set that an alarm for the situation in which the driver is not looing forward is provided based on the image in addition to the above-described carelessness alarm based on the electroencephalogram of the driver.

The above detailed description is to be construed in all aspects as illustrative and not restrictive. The scope of the present disclosure should be determined by reasonable interpretation of the appended claims and all changes coming within the equivalency range of the present disclosure are intended to be embraced in the scope of the present disclosure.

INDUSTRIAL APPLICABILITY

The electroencephalogram-based driver assistance system and assistance method according to the embodiments of the present disclosure as described above may be utilized by being applied to the vehicle that regularly operates on the determined moving path, such as the bus and a truck. Additionally, such concept does not necessarily have to be limited to being applied only to the vehicle, and is able to be applied to various mobilities.

What is claimed is:

1. A system for assisting a driver using an electroencephalogram, the system comprising:

an electroencephalogram measurer configured to measure an electroencephalogram signal of the driver;

a mobile terminal configured to receive the measured electroencephalogram signal and to output a careless state of the driver determined based on the received electroencephalogram signal via an app; and a controller configured to control a vehicle based on the determined careless state of the driver and to provide an alarm to the driver, wherein the mobile terminal includes a processor configured to analyze a frequency component in the received electroencephalogram signal and to quantify the careless state of the driver using the analyzed frequency component, wherein the processor is configured to analyze the frequency component in the received electroencephalogram signal via a window size in a first time unit, and wherein the processor is configured to shift the window size into a second time unit on a time axis and analyze the frequency component based on the window size.

2. The system of claim 1, wherein the processor is configured to analyze the frequency component by classifying the frequency component by performing Fourier transform on the received electroencephalogram signal, wherein the classified frequency component includes at least one of theta, beta, or SMR frequencies.

3. The system of claim 2, wherein the processor is configured to use the classified frequency component to quantify the careless state of the driver into a numerical value.

4. The system of claim 3, wherein the processor is configured to determine the careless state of the driver by comparing the numerical value with a preset alertness value.

5. The system of claim 1, wherein the mobile terminal is configured to output at least one of an emoji, a text, a color, and the received electroencephalogram signal via the app.

6. The system of claim 5, wherein the mobile terminal is configured to output a navigation screen or a number of alarms provided to the driver via the app.

7. The system of claim 1, wherein the controller is configured to provide the alarm to the driver by controlling the vehicle, including at least one of a display, an interior light, an air conditioner, a seat, and a speaker of the vehicle.

8. A system for assisting a driver using an electroencephalogram, the system comprising:

a wearable device configured to measure an electroencephalogram signal of the driver;

a mobile terminal equipped with an app, wherein the app is configured to:

receive the electroencephalogram signal measured by the wearable device and a driving information signal acquired from a mobility;

process the received electroencephalogram signal and driving information signal and provide the processed electroencephalogram signal and driving information signal to a server; and receive carelessness alarm information converted into big data from the server; and a controller configured to control the mobility based on the carelessness alarm information and to provide a carelessness-related alarm to the driver, wherein the driving information signal includes at least one of a GPS signal, a moving path signal of the mobility, a time information signal, and a weather information signal, wherein the carelessness alarm information includes at least one of information on in which moving path or location carelessness occurs, information on in what time period the carelessness occurs, and information on under what weather the carelessness occurs.

9. The system of claim 8, wherein the carelessness alarm information includes driving information acquired from a plurality of mobilities and information determined based on an electroencephalogram signal for each driving information.

10. The system of claim 8, wherein the controller is configured to provide the carelessness-related alarm to the driver based on at least one of a moving path, a time, and a weather corresponding to the carelessness alarm information.

11. The system of claim 8, wherein the wearable device includes:

a measurer wearable on a left ear of the driver; and a functional member including a battery configured to supply power to the measurer, wherein the functional member is fixable to a body part other than the ear of the driver or a fixture.

12. The system of claim 8, wherein the app is configured to:

measure electroencephalogram characteristics of the driver using an electroencephalogram signal measured during a predetermined time period while the driver wears the wearable device and drives; and measure an electroencephalogram signal after the predetermined time period in consideration of the electroencephalogram characteristics of the driver.

13. A method for assisting a driver using an electroencephalogram, the method comprising:

measuring, by an electroencephalogram measurer, an electroencephalogram signal of the driver;

receiving, by a mobile terminal, the measured electroencephalogram signal and determining a careless state of the driver based on the received electroencephalogram signal;

outputting, by an app installed on the mobile terminal, the determined careless state of the driver; and controlling, by a controller, a vehicle based on the determined careless state of the driver and providing an alarm to the driver, wherein the determining of the careless state of the driver includes analyzing a frequency component in the received electroencephalogram signal and quantifying the careless state of the driver using the analyzed frequency component, wherein the determining of the careless state of the driver includes analyzing the frequency component in the received electroencephalogram signal via a window size in a first time unit, and wherein the window size is shifted into a second time unit on a time axis and the frequency component is analyzed based on the window size.

14. The method of claim 13, wherein the analyzing of the frequency component includes classifying the frequency component by performing Fourier transform on the received electroencephalogram signal, wherein the classified frequency component includes at least one of theta, beta, and SMR frequencies.

* * * * *